United States Patent
Sacurai et al.

(10) Patent No.: US 9,359,378 B2
(45) Date of Patent: Jun. 7, 2016

(54) SUBSTITUTED OXAZOLO[3,4-A]PYRAZINES AS PHARMACEUTCALS

(71) Applicant: BIOLAB SANUS FARMACÊUTICA LTDA., Taboão de Serra (BR)

(72) Inventors: Sérgio Luiz Sacurai, São Paulo (BR); Carlos Eduardo Da Costa Touzarim, São Paulo (BR); Fabiano Travanca Toledo, Osasco (BR); Bruno Artur De Sousa, São Paulo (BR)

(73) Assignee: BIOLAB SANUS FARMACEUTICA LTDA., Taboao De Serra (BR)

( * ) Notice: Subject to any disclaimer, the term of this patent is extended or adjusted under 35 U.S.C. 154(b) by 0 days.

(21) Appl. No.: 14/630,410

(22) Filed: Feb. 24, 2015

(65) Prior Publication Data

US 2015/0239903 A1    Aug. 27, 2015

Related U.S. Application Data

(60) Provisional application No. 61/943,825, filed on Feb. 24, 2014.

(51) Int. Cl.
| | |
|---|---|
| *A61K 31/4985* | (2006.01) |
| *C07D 241/38* | (2006.01) |
| *C07D 498/04* | (2006.01) |
| *C07D 413/14* | (2006.01) |

(52) U.S. Cl.
CPC ............ *C07D 498/04* (2013.01); *C07D 413/14* (2013.01)

(58) Field of Classification Search
CPC .......................... A61K 31/4985; C07D 241/38
USPC ............ 514/249; 544/350; 548/455; 549/434
See application file for complete search history.

(56) References Cited

U.S. PATENT DOCUMENTS 8,338,432 B2 * 12/2012 Sacurai et al. ............ 514/255.05

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Hackam, et al. JAMA, 296(14), 2006, 1731-1732.*

* cited by examiner

*Primary Examiner* — Douglas M Willis
(74) *Attorney, Agent, or Firm* — Arent Fox LLP

(57) ABSTRACT

The present invention relates to novel derivatives of 6,7-dihydro-3H-oxazolo[3,4-a]pyrazine-5,8-dione represented by formula (I):

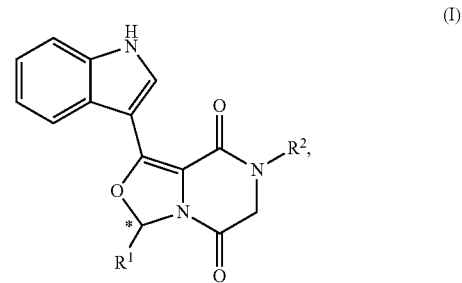

and a mixture of these derivatives. The present invention also encompasses the pharmaceutical compositions comprising an effective amount of a said compounds, object of the present invention, as well as to the use of the compounds and/or derivatives as a phosphodiesterase enzyme inhibitor, and the use of the compounds and/or derivatives in the treatment of erectile dysfunction, disorders and/or conditions treatable with relaxation of tissues and disorders treatable with phosphodiesterase inhibitors, more particularly PDE-5 inhibitor. A further objective of the present invention is to provide a medication comprising a therapeutically effective amount of said compound and a method of treating using the said novel compounds.

10 Claims, 11 Drawing Sheets

PE (1μm)    DMSO

PE (1μm)    Tadalafil (1μm)

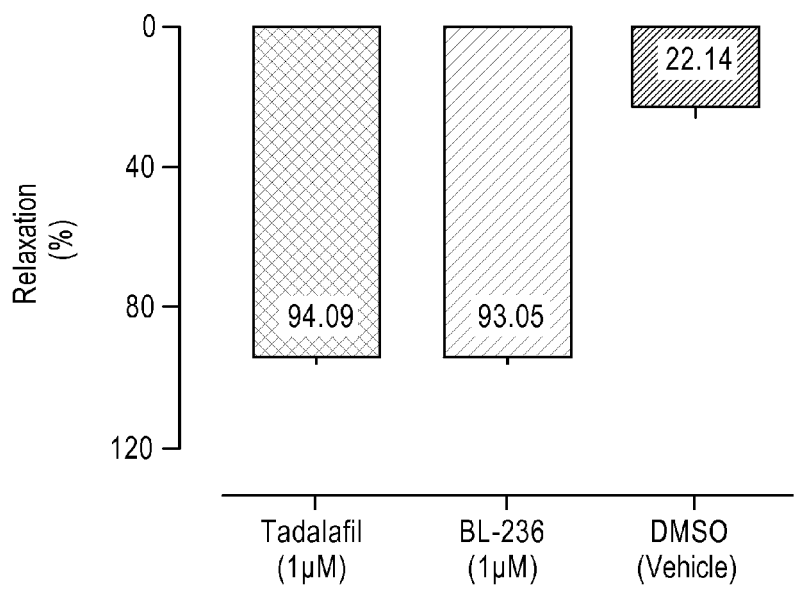
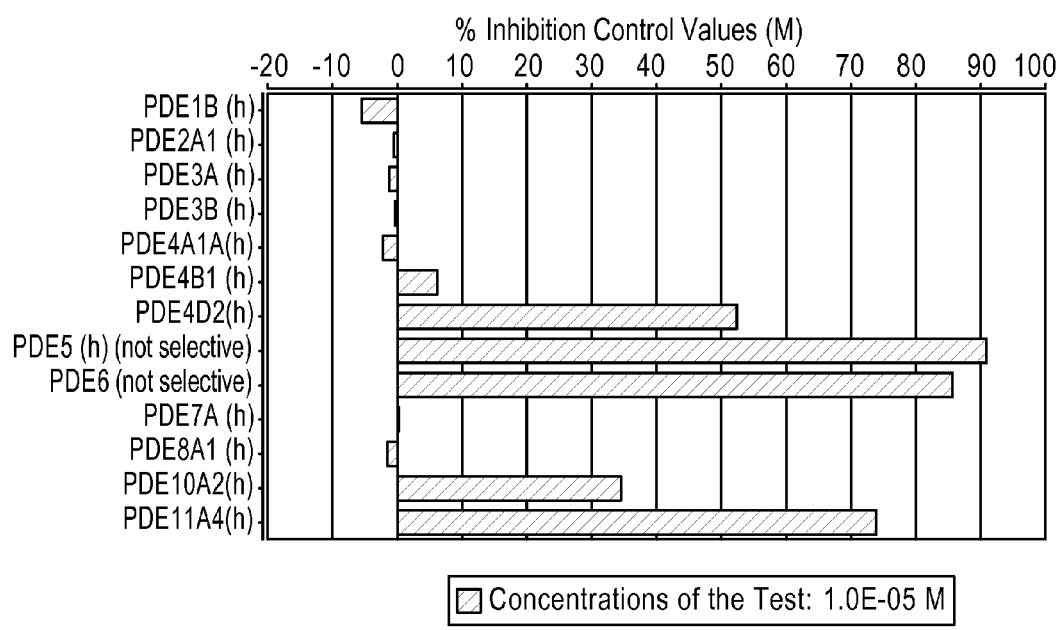

SUBSTITUTED OXAZOLO[3,4-A]PYRAZINES AS PHARMACEUTCALS

FIELD OF THE INVENTION

The present invention relates to novel derivatives of 6,7-dihydro-3H-oxazolo[3,4-a]pyrazine-5,8-dione, a mixture of these derivatives (in any proportion), including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion; the processes of preparation of said compounds and/or derivatives thereof.

The present invention also encompasses the pharmaceutical compositions comprising said novel compound derivatives of 6,7-dihydro-3H-oxazolo[3,4-a]pyrazine-5,8-dione, the mixture of these derivatives (in any proportion) including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion; medications comprising said compounds and/or derivatives, as well as to the use of the compounds and/or derivatives as a phosphodiesterase enzyme inhibitor, more particularly as a phosphodiesterase type 5 (PDE-5) inhibitor; and the use of the compounds and/or derivatives in the treatment of erectile dysfunction, disorders and/or conditions treatable with tissues relaxation and disorders treatable with phosphodiesterase inhibitors, more particularly PDE-5 inhibitor.

The present invention also discloses a method of treating erectile dysfunction, disorders and/or conditions treatable with tissues relaxation and disorders treatable with phosphodiesterase inhibitors, specifically as PDE-5 inhibitors, using the novel compounds derived from 6,7-dihydro-3H-oxazolo[3,4-a]pyrazine-5,8-dione, a mixture of these derivatives (in any proportion), including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion.

In particular, the present invention discloses the compounds named 3-(benzo[d][1,3]dioxol-5yl)-7-(2-hydroxyethyl)-1-(1H-indol-3-yl)-6,7-dihydro-3H-oxazolo[3,4-a]pyrazine-5,8-dione (BL-230); and 3-(benzo[d][1,3]dioxol-5yl)-7-((S)1-hydroxypropan-2yl)-1-(1H-indol-3-yl)-6,7-dihydro-3H-oxazolo[3,4-a]pyrazine-5,8-dione (BL-236).

BACKGROUND OF THE INVENTION

The phosphodiesterase inhibitor compounds are the main agents used in clinical medicine for treatment and/or prevention of erectile dysfunction, disorders and/or treatable conditions with tissues relaxation and other diseases treatable with phosphodiesterase inhibitors. In the case of erectile dysfunction, PDE-5 inhibitors are the most widely used in clinical medicine.

Erectile dysfunction, more commonly known as sexual impotence is one of the diseases that most affect a man's quality of life. For a long time, erectile dysfunction haunted men without considerable chances for effective treatment.

Before the 1970s, almost all cases of erectile dysfunction were considered resulting from psychological causes, and treatments consisted of empirical administration of testosterone or referral to a psychiatrist. The development of new treatments such as inflatable penile prostheses, developed in 1973 and the emergence of intracavernous injections, in early 1980, were important milestones in the history of modern erectile dysfunction treatments. The first treatment of oral use, based on sildenafil citrate (Viagra's active ingredient) was released in 1998 and was an important milestone for erectile dysfunction treatments.

Oral treatment is more accepted by men, developed through clinical research on the use of cGMP-PDE inhibitors, more particularly PDE-5 inhibitors. The precursor of these compounds was 5-{2-Ethoxy-5-[(4-methyl-1-piperazinyl)sulfonyl]phenyl}-1-methyl-3-propyl-1,4-dihydro-7H-pyrazolo[4,3-d]pyrimidin-7-one, or sildenafil, with vasodilating properties, and which enhances the nitric oxide effects. The Sildenafil molecule was originally described in U.S. Pat. No. 5,250,534.

Later, other inhibitor compounds of the enzyme PDE-5 were developed and are cited in a number of technical literature publications, as well as in patent publications. Among the known compounds include: the molecule of vardenafil, Levitra's active ingredient, first described in the U.S. Pat. No. 3,635,178; tadalafil, Cialis's active ingredient, first described in U.S. Pat. No. 5,859,006; and the compound BL-106, not yet commercialized, first described in U.S. Pat. No. 8,338,432 and developed by the same team of present invention's researchers.

Available studies report that some form of sexual dysfunction affects 10-52% of men. The study by Feldman and his colleagues have shown that 52% of men between the ages of 40 and have mild, moderate and severe degrees of erectile dysfunction. Between the ages of 40 and 70, the prevalence of mild erectile dysfunction remains relatively constant, but the prevalence of moderate to severe erectile dysfunction increases with each decade with the total combined increase progressing from 40% at age 40 years to almost 70% at 70 years (Feldman H A, Goldstein I, Hatzichristou D G, et al. *Impotence and its medical and psychosocial correlates: results of the Massachusetts Male Aging Study. J Urol* 1994; 151: 54-61).

Additionally, the researchers found that tissue relaxing compounds have been used to promote relaxation of various tissues with a focus on treating or acting as an aid in the treatment, procedure or related surgery of gallstones (Korkes, F. et al, J Bras Nefrol. (2009) 31 (1): 55), increased prostate (e.g., benign prostatic hyperplasia, prostatitis) (WO 9911279) and urethral constriction (Van der Werf et al BJU International (2002) 90: 588). Other disorders and/or conditions treatable with tissue relaxation are known and described in the art.

PDE-5 inhibitors have been used to block the degradation of cGMP to prolong nitric oxide (NO) effects in various tissues, for example, to maintain the NO-induced relaxation in airways and blood vessels (Barnes, P J, et al., (1995) and to maintain the NO-induced protection in tissue (Duffin, R., et al., Br J Pharmacol. (2008) 153(4): 623. Such actions in the tissues are shown to be beneficial for the treatment of several disorders—disorders which are treatable with inhibitors of phosphodiesterases, particularly PDE-5, including pulmonary hypertension (commercially treated with sildenafil citrate); bronchitis; chronic asthma; hypertension (EP758653, U.S. Pat. No. 7,569,572); Raynaud's disease (Ghofrani H A et al, Nat Rev Drug Discov 2006; 5:689); the onset of right-sided heart failure (Ghofrani et al. (2003) AJRCCM 167 (8): 1139); neurogenesis and functional recovery post stroke (Zhang et al. (2002) Stroke 33: 2675-2680); coronary artery relaxation (Halcox et al. (2002) J Am Coll Cardiol 40: 1232); disorders of female sexual arousal (Nehra et al. (2001) World J Urol. 19 (1): 115); angina and congestive heart failure (Reffelmann et al., Circ. (2003) 108(2):239). Other disorders treatable with PDE-5 inhibitors are known and described in the art.

Within this framework and seeking new alternatives of phosphodiesterase inhibitor compounds, more specifically as PDE-5 inhibitors, new treatments for erectile dysfunction, disorders and/or conditions treatable with tissues relaxation and other diseases treatable with phosphodiesterase inhibitors, the present invention's researchers have developed new compounds derived from 6,7-dihydro-3H-oxazolo[3,4-a] pyrazine-5,8-dione, object of the present invention, which present enzymes' phosphodiesterase inhibitory activity, including inhibition of PDE-5.

SUMMARY OF THE INVENTION

The present invention aims to provide new compounds derived from 6,7-dihydro-3H-oxazolo[3,4-a]pyrazine-5,8-dione, a mixture of these derivatives (in any proportion), including salts, solvates, hydrates, prodrugs and pharmaceutically acceptable esters; enantiomers and/or diastereoisomers of the compounds separated in their individual forms and/or in its racemic or non-racemic mixtures forms with enantiomeric excess in any proportion. More specifically the compounds referred to as 3-(benzo[d][1,3]dioxol-5yl)-7-(2-hydroxyethyl)-1-(1H-indol-3-yl)-6,7-dihydro-3H-oxazolo [3,4-a]pyrazine-5,8-dione (BL-230); and 3-(benzo[d][1,3]dioxol-5yl)-7-((S)1-hydroxypropan-2yl)-1-(1H-indol-3-yl)-6,7-dihydro-3H-oxazolo[3,4-a]pyrazine-5,8-dione (BL-236); and/or a mixture of such compounds (in any proportion).

Another aspect of the present invention is the use of compounds derived from 6,7-dihydro-3H-oxazolo[3,4-a]pyrazine-5,8-dione, object of the present invention, for the curative and/or prophylactic treatment of erectile dysfunction, disorders and/or conditions treatable with tissues relaxation and disorders treatable with phosphodiesterases inhibitors, specifically with PDE-5 inhibitors.

It is also the objective of this invention to provide processes for preparing the novel compounds derived from 6,7-dihydro-3H-oxazolo[3,4-a]pyrazine-5,8-dione, object of the present invention. In particular, processes for the preparation of the compounds 3-(benzo[d][1,3]dioxol-5yl)-7-(2-hydroxyethyl)-1-(1H-indol-3-yl)-6,7-dihydro-3H-oxazolo[3,4-a] pyrazine-5,8-dione (BL-230); and 3-(benzo[d][1,3]dioxol-5yl)-7-((S)1-hydroxypropan-2yl)-1-(1H-indol-3-yl)-6,7-dihydro-3H-oxazolo[3,4-a]pyrazine-5,8-dione (BL-236); and/or mixtures of these compounds (in any proportion).

Furthermore, the present invention also aims to provide pharmaceutical compositions comprising an effective amount of a compound of new derivatives of 6,7-dihydro-3H-oxazolo[3,4-a]pyrazine-5,8-dione, or mixture of these derivatives (in any proportion), including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion.

In particular, pharmaceutical compositions comprising at least one of the novel compounds derived from 6,7-dihydro-3H-oxazolo[3,4-a]pyrazine-5,8-dione, selected from: 3-(benzo[d][1,3]dioxol-5yl)-7-(2-hydroxyethyl)-1-(1H-indol-3-yl)-6,7-dihydro-3H-oxazolo[3,4-a]pyrazine-5,8-dione (BL-230); and 3-(benzo[d][1,3]dioxol-5yl)-7-((S)1-hydroxypropan-2yl)-1-(1H-indol-3-yl)-6,7-dihydro-3H-oxazolo[3,4-a]pyrazine-5,8-dione (BL-236); or a mixture of these derivatives (in any proportion), including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion.

A further objective of the present invention is to provide a medication comprising a therapeutically effective amount of a compound of new derivatives of 6,7-dihydro-3H-oxazolo [3,4-a]pyrazine-5,8-dione, mixtures of these derivatives (in any proportion), including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion. In particular, medications comprising at least one of the novel compounds derived from 6,7-dihydro-3H-oxazolo[3,4-a]pyrazine-5,8-dione, selected from: 3-(benzo[d][1,3]dioxol-5yl)-7-(2-hydroxyethyl)-1-(1H-indol-3-yl)-6,7-dihydro-3H-oxazolo[3,4-a]pyrazine-5,8-dione (BL-230); and 3-(benzo[d][1,3]dioxol-5yl)-7-((S)1-hydroxypropan-2yl)-1-(1H-indol-3-yl)-6,7-dihydro-3H-oxazolo[3,4-a]pyrazine-5,8-dione (BL-236); and/or a mixture of such compounds (in any proportion).

BRIEF DESCRIPTION OF THE FIGURES

FIG. 13 shows a bar graph with the percentage of relaxation in rabbit's corpus cavernosum when BL-236, tadalafil and DMSO (solvent) were given.

FIG. 14 shows the percentage of phosphodiesterase enzyme inhibition observed in the presence of the BL-230 compound.

DETAILED DESCRIPTION OF THE INVENTION

Figure 1:
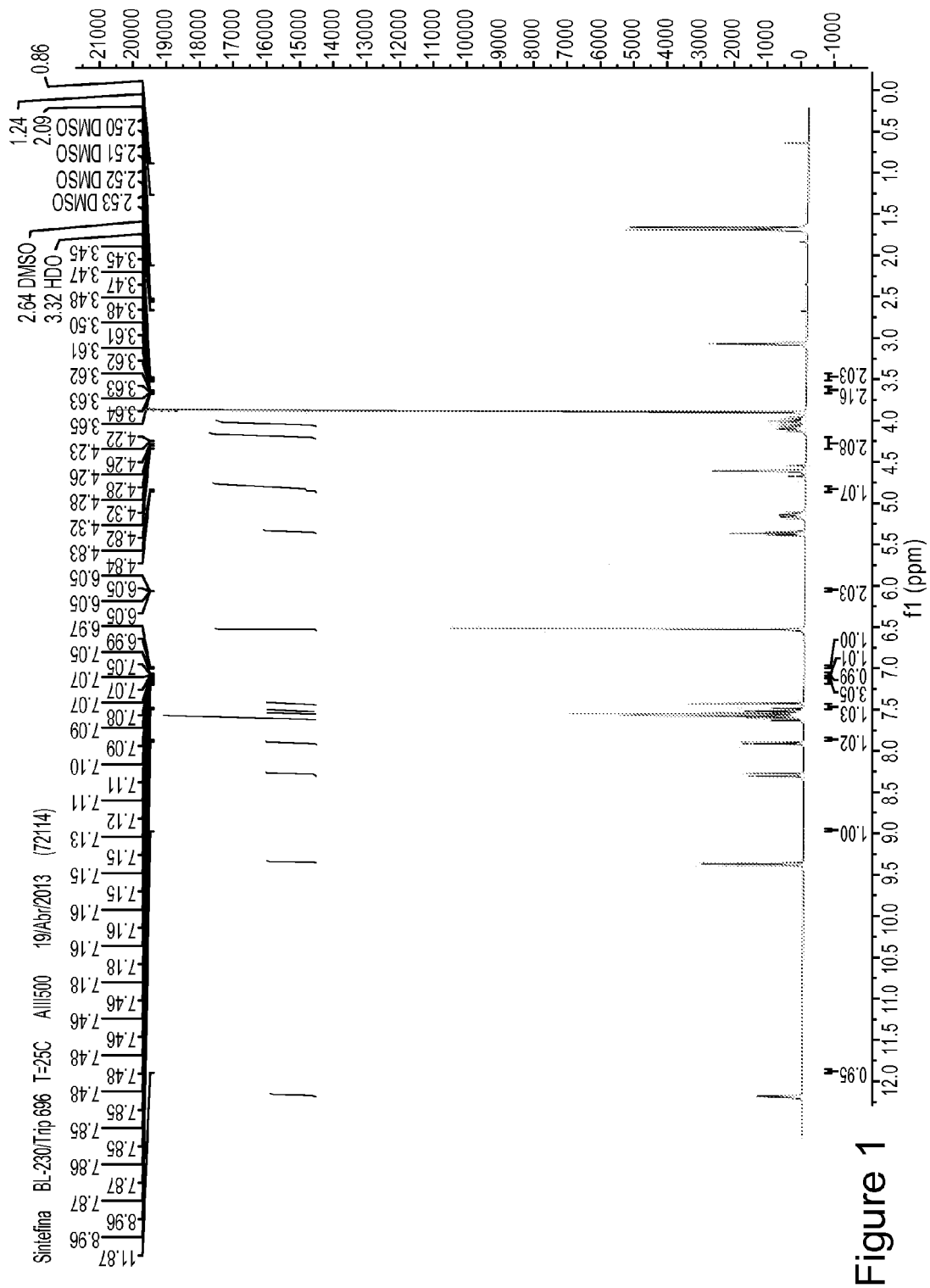
FIG. 1 shows the $^1$H NMR spectrum for the characterization of the compound obtained in Example 1 (BL-230).

The present invention discloses novel compounds useful for the treatment of diseases treatable with phosphodiesterase inhibitors, especially for the inhibition of PDE-5, for example, erectile dysfunction, disorders and/or conditions treatable with tissues relaxation and other diseases treatable with phosphodiesterase inhibitors. The compounds of the present invention refer to new compounds derived from 6,7-dihydro-3H-oxazolo[3,4-a]pyrazine-5,8-dione represented by the formula (I):

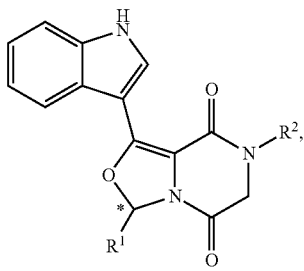
(I)

where:

R¹ is aryl, heteroaryl, 2-hydroxyphenyl, 3-hydroxyphenyl, 4-hydroxyphenyl, 3-methoxy-4-hydroxyphenyl, 2-methoxyphenyl, 3-methoxyphenyl, 4-methoxyphenyl, 3,4-dimethoxyphenyl, 2-halophenyl, 3-halophenyl or 4-halophenyl furyl; pyridine, aromatic bicyclic, aromatic bicyclic containing one or more heteroatoms;

R² is aryl, heteroaryl, bicicloaryl, $CH_2$ $(CH_2)_n R^3$, $CH_2$ $(CH_2)_n NR^4 R^5$, $CHR^6 CH_2 OH$, $CH_2 CH(OH)$ $R^7$, $CH_2$ $(CH_2)_n$ $OR^B$, $CH_2$ $(CH_2)_n$ $SR^9$, carboxylate salts, sulfonate salts or quaternary ammonium salts;

R³ is OH, $NH_2$, $NH^{3+}$, S(O)Me, $SO_3 H$, $CO_2 H$, Cl, carboxylate salts, sulfonate salts or quaternary ammonium salts;

R⁴ is hydrogen, methyl, ethyl, propyl, i-propyl, butyl, sec-butyl, tert-butyl, phenyl, benzyl or quaternary ammonium salts;

R⁵ is hydrogen, methyl, ethyl, propyl, i-propyl, butyl, sec-butyl, tert-butyl, phenyl, benzyl or quaternary ammonium salts;

R⁶ is methyl, ethyl, isopropyl, isobutyl, sec-butyl, phenyl, benzyl, $CH_2 SH$, $CH_2 CH_2 SCH_3$ or $CH_2 OH$;

R⁷ is methyl, ethyl, propyl, phenyl or benzyl;

R⁸ is $C_{1-6}$ alkyl, $C_{2-6}$ alkenyl, $C_{2-6}$ alkynyl, phenyl or benzyl;

R⁹ is $C_{1-6}$ alkyl, $C_{2-6}$ alkenyl, $C_{2-6}$ alkynyl, phenyl or benzyl;

N is 0, 1, 2, 3 or 4;

the mixture of these derivatives (in any proportion), including salts, solvates, hydrates, prodrugs and pharmaceutically acceptable esters.

The compounds of formula (I) may contain one or more chiral centers and, therefore, enantiomers and/or diastereomers may exist. In particular, a chiral center is highlighted with an asterisk (*) in the description of formula (I). Therefore, the present invention also encompasses the enantiomers and/or diastereomers of the compounds of formula (I) separated in their individual forms and/or in the forms of racemic or non-racemic mixtures with enantiomeric excess in any proportion.

The compounds of formula (I) can exist in two tautomeric forms, and the invention includes one or more tautomeric forms and mixtures of these forms (in any proportion).

Pharmaceutically acceptable salts of the compounds of formula (I) are formed by adding pharmaceutically acceptable acids. Examples of salts include, but are not limited to salts of: nitrate, hydrochloride, hydrobromide, sulfate or bisulfate, phosphate, hydrogen phosphate, acetate, benzoate, succinate, fumarate, maleate, lactate, citrate, tartrate, gluconate, methanesulfonate, benzenesulfonate and p-toluenesulfonate. The compounds of formula (I) may be used in pharmaceutically acceptable metal salts, in particular alkali metal salts, with bases such as sodium and potassium salts.

In a specific embodiment, the present invention describes new compounds derived from 6,7-dihydro-3H-oxazolo[3,4-a]pyrazine-5,8-dione represented by formula (I):

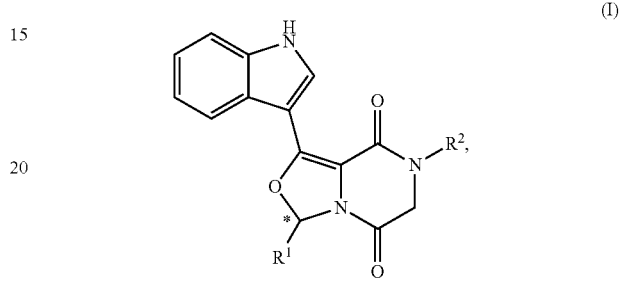
(I)

where:

R¹ is benzo[d][1,3]dioxolyl;

R² is $CH_2$ $(CH_2)_n R^3$ or $CHR^6 CH_2 OH$;

R³ is OH;

R⁶ is methyl;

N is 1;

the mixture of these derivatives (in any proportion), including salts, solvates, hydrates, prodrugs and pharmaceutically acceptable esters; enantiomers and/or diastereoisomers of the compounds separated in their individual forms and/or in the forms of racemic mixtures or non-racemic enantiomeric excess in any proportion.

In a more specific embodiment, the novel compounds derived from 6,7-dihydro-3H-oxazolo[3,4-a]pyrazine-5,8-dione, are represented by the following formulas:

Formula (II):

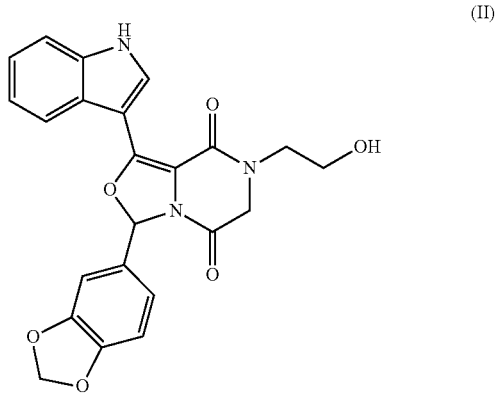 [SMILES: O=C1C2=C(c3c[nH]c4ccccc34)OC(c3ccc4c(c3)OCO4)N2C(=O)CN1CCO]
(II)

Referred to as 3-(benzo[d][1,3]dioxol-5yl)-7-(2-hydroxyethyl)-1-(1H-indol-3-yl)-6,7-dihydro-3H-oxazolo[3,4-a]pyrazine-5,8-dione (BL-230); and Formula (III):

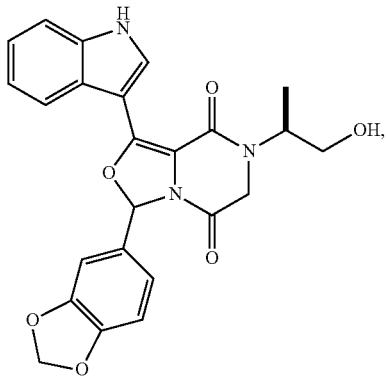

Referred to as 3-(benzo[d][1,3]dioxol-5yl)-7-((S)1-hydroxypropan-2yl)-1-(1H-indol-3-yl)-6,7-dihydro-3H-oxazolo[3,4-a]pyrazine-5,8-dione (BL-236);

or a mixture of these derivatives (in any proportion), including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion.

In another embodiment of the present invention, it refers to the synthetic process of the compound of formula (II) called 3-(benzo[d][1,3]dioxol-5yl)-7-(2-hydroxyethyl)-1-(1H-indol-3-yl)-6,7-dihydro-3H-oxazolo[3,4-a]pyrazine-5,8-dione (BL-230), which can be obtained using the compounds (E)-methyl 2-((benzo[d][1,3]dioxol-5-ylmethylene)amino)-3-(1H-indol-3-yl)-3-oxopropanoate described by the chemical structure (a); methyl 2-(benzo[d][1,3]dioxol-5-yl)-3-(2-chloroacetyl)-5-(1H-indol-3-yl)-2,3-dihydrooxazole-4-carboxylate described by the chemical structure (b) and the amine 2-aminoethanol described by the chemical structure (c).

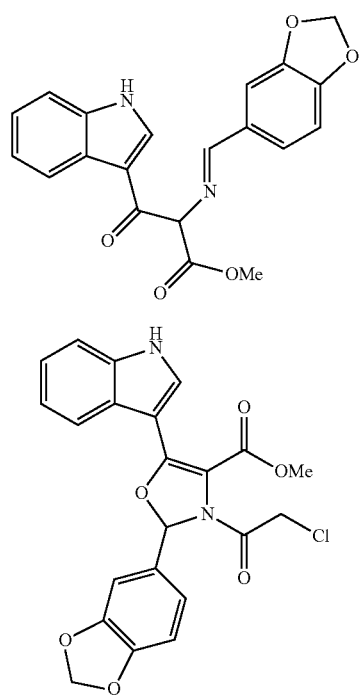

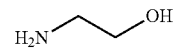

For the synthesis of the compound of formula (II), compound (b) is prepared by reacting compound (a) in the presence of a dry solution of pyridine (Py) in tetrahydrofuran (THF) and chloroacetyl chloride solution. After completion of the reaction to form the intermediate (b), this is added to the medium with ethanol and 2-aminoethanol (c) at the end of the reaction, ethanol and water are added, resulting in obtaining the compound of formula (II) as illustrated in Scheme [1]:

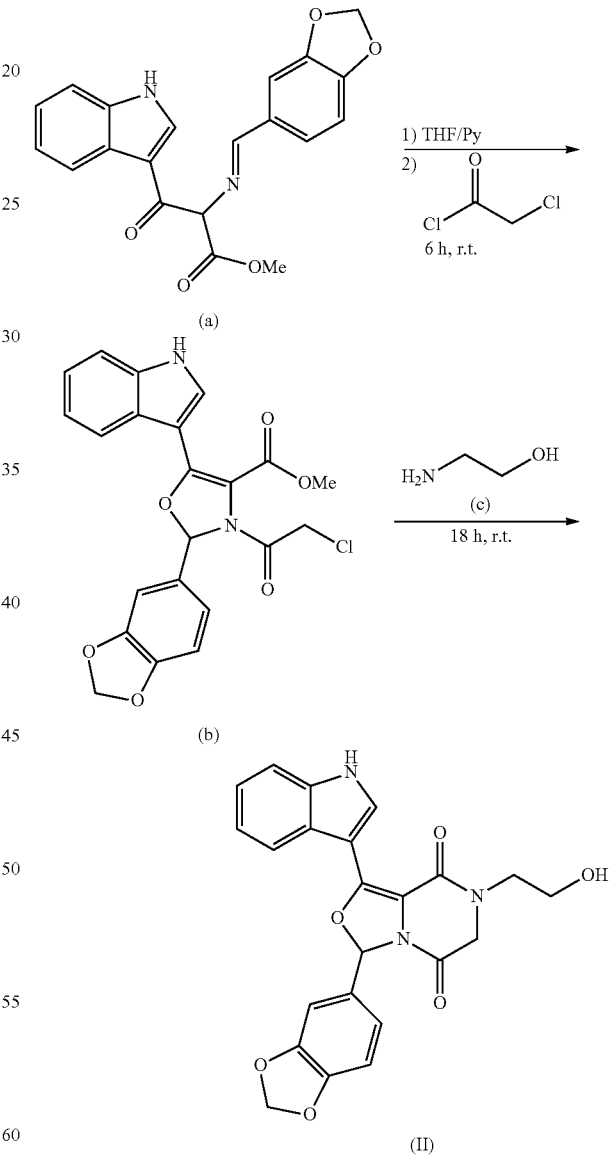

Since the compound of formula (III), referred to as 3-(benzo[d][1,3]dioxol-5yl)-7-((S)1-hydroxypropan-2yl)-1-(1H-indol-3-yl)-6,7-dihydro-3H-oxazolo[3,4-a]pyrazine-5,8-dione (BL-236), according to the present invention, can be obtained using the compounds (E)-methyl 2-((benzo[d][1,3]

dioxol-5-ylmethylene)amino)-3-(1H-indol-3-yl)-3-oxopropanoate described by the chemical structure (a) methyl 2-(benzo[d][1,3]dioxol-5-yl)-3-(2-chloroacetyl)-5-(1H-indol-3-yl)-2,3-dihydrooxazole-4-carboxylate described by the chemical structure (b) and the amine(S)-2-aminopropan-1-ol as described by the chemical structure (d).

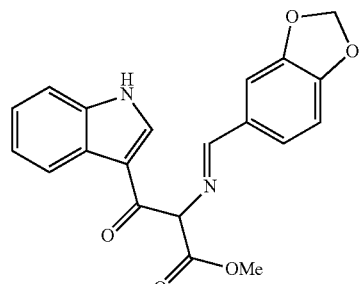

(a)

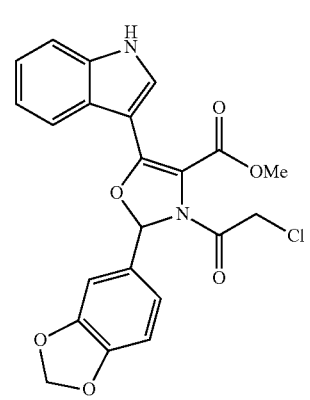

(b)

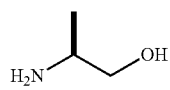

(d)

For the synthesis of the compound of formula (III), compound (b) is prepared by reacting compound (a) in the presence of a dry solution of pyridine (Py) in tetrahydrofuran (THF) and chloroacetyl chloride solution. After completion of the reaction to form the intermediate (b), this is added to the medium the ethyl alcohol and (S)-2-aminopropan-1-ol (d) at the end of the reaction, ethanol and water are added, resulting in obtaining the compound of Formula (III) as shown in Scheme [2]:

[2]

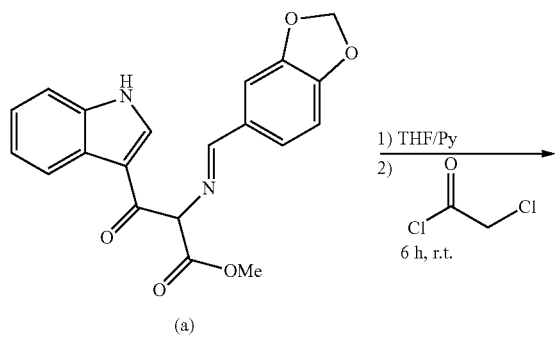

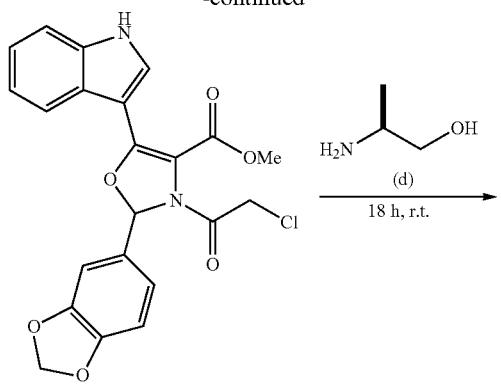

(b)

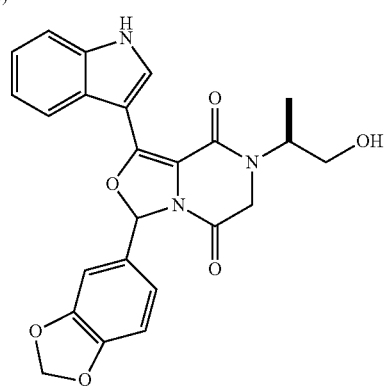

(III)

The present invention also contemplates pharmaceutical compositions, i.e., an appropriate dosage form wherein said composition comprises as an active ingredient an effective amount of one or more compounds of formula (I), including salts, solvates, hydrates, prodrugs and pharmaceutically acceptable esters; enantiomers and/or diastereoisomers of the compounds separated in their individual forms and/or in the form of racemic or non-racemic mixtures with enantiomeric excess in any proportion.

Preferably, the compositions of the invention comprise as an active ingredient the novel compounds that are represented by the following formulas:

Formula (II):

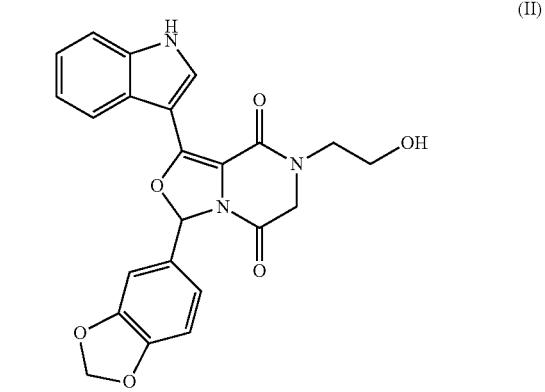 [SMILES: O=C1C2=C(c3c[nH]c4ccccc34)OC(c3ccc4c(c3)OCO4)N2C(=O)CN1CCO]

(II)

referred to as 3-(benzo[d][1,3]dioxol-5yl)-7-(2-hydroxy-ethyl)-1-(1H-indol-3-yl)-6,7-dihydro-3H-oxazolo[3,4-a]pyrazine-5,8-dione (BL-230); and Formula (III):

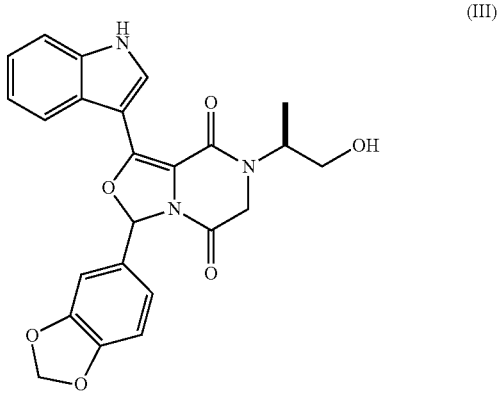 [SMILES: C[C@@H](CO)N1CC(=O)N2C(=C(c3c[nH]c4ccccc34)OC2c2ccc3c(c2)OCO3)C1=O]

referred to as 3-(benzo[d][1,3]dioxol-5yl)-7-((S)1-hydroxypropan-2yl)-1-(1H-indol-3-yl)-6,7-dihydro-3H-oxazolo[3,4-a]pyrazine-5,8-dione (BL-236);
or a mixture of these derivatives (in any proportion), including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion.

The pharmaceutical compositions may be prepared by well-known methods in the art. Suitably, Remington's Pharmaceutical Sciences or similar sources of information can be used to prepare a suitable pharmaceutical formulation for a carrier compound of the invention.

The pharmaceutical compositions of the present invention may be administered by oral, topical, injectable, nasal, and rectal means. The particular mode selected will depend on the compounds present in the composition.

The pharmaceutical compositions for oral administration can be presented, but not limited to: powders, granules, capsules, tablets, effervescent tablets, chewable tablets, coated tablets, pills, gels, chewable gums, films, solutions, syrups, elixirs, suspensions, emulsions, and the like.

The present invention also contemplates pharmaceutical compositions comprising a therapeutically effective amount of one or more compounds of formula (I) and/or salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion; and one or more pharmaceutically acceptable excipients.

In particular, pharmaceutical compositions comprising as an active ingredient at least one of the following compounds selected from the group consisting of:
(a) 3-(benzo[d][1,3]dioxol-5yl)-7-(2-hydroxyethyl)-1-(1H-indol-3-yl)-6,7-dihydro-3H-oxazolo[3,4-a]pyrazine-5,8-dione (BL-230) described in formula (II)
(b) 3-(benzo[d][1,3]dioxol-5yl)-7-((S)1-hydroxypropan-2yl)-1-(1H-indol-3-yl)-6,7-dihydro-3H-oxazolo[3,4a]pyrazine-5,8-dione (BL-236) described in formula (III);
a mixture thereof in any proportion, including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion; and one or more pharmaceutically acceptable excipients.

The compounds described herein, including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion; are employed for the treatment and/or prophylaxis of erectile dysfunction, disorders and/or conditions treatable with tissues relaxation and disorders treatable with phosphodiesterase inhibitors such as PDE-5. The disorders treatable by PDE inhibitors may be lithiasis, prostatic hyperplasia, pulmonary hypertension, urethral constriction, female sexual dysfunction and/or male sexual dysfunction, but not limited to these examples only.

Additionally, the present invention contemplates pharmaceutical compositions comprising the compounds described herein, including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion; are employed for the treatment and/or prophylaxis of erectile dysfunction, disorders and/or conditions treatable with tissues relaxation and disorders treatable with phosphodiesterase inhibitors such as PDE-5. The disorders treatable by PDE inhibitors may be lithiasis, prostatic hyperplasia, pulmonary hypertension, urethral constriction, female sexual dysfunction and/or male sexual dysfunction, but not limited to these examples only.

In particular, the compounds 3-(benzo[d][1,3]dioxol-5yl)-7-(2-hydroxyethyl)-1-(1H-indol-3-yl)-6,7-dihydro-3H-oxazolo[3,4-a]pyrazine-5,8-dione (BL-230) described in formula (II), and 3-(benzo[d][1,3]dioxol-5yl)-7-((S)1-hydroxypropan-2yl)-1-(1H-indol-3-yl)-6,7-dihydro-3H-oxazolo[3,4-a]pyrazine-5,8-dione (BL-236) described in formula (III); or a mixture of these derivatives (in any proportion), including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion.

Additionally, the present invention provides a method of treatment and/or prevention of disorders associated with the activity of phosphodiesterases, administering an effective dose of at least one of the new compounds derived from 6,7-dihydro-3H-oxazolo[3,4-a]pyrazine-5,8-dione, a mixture of these derivatives (in any proportion), including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion. The disorders treatable by PDE inhibitors may be erectile dysfunction, gallstones, prostatic hyperplasia, pulmonary hypertension, urethral constriction, female sexual dysfunction and/or male sexual dysfunction, but not limited to these examples only.

The present invention also discloses a method of treatment and/or prevention of erectile dysfunction, disorders and/or conditions treatable with tissues relaxation and disorders treatable with phosphodiesterase inhibitors such as PDE-5 by administering an effective dose of at least one of the new compounds derived from 6,7-dihydro-3H-oxazolo[3,4-a]

pyrazine-5,8-dione, a mixture of these derivatives (in any proportion), including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion.

In particular, the compounds 3-(benzo[d][1,3]dioxol-5yl)-7-(2-hydroxyethyl)-1-(1H-indol-3-yl)-6,7-dihydro-3H-oxazolo[3,4-a]pyrazine-5,8-dione (BL-230-formula II); and: 3-(benzo[d][1,3]dioxol-5yl)-7-((S)1-hydroxypropan-2yl)-1-(1H-indol-3-yl)-6,7-dihydro-3H-oxazolo[3,4-a]pyrazine-5,8-dione (BL-236-Formula III); or a mixture of these derivatives (in any proportion), including salts, solvates, hydrates, prodrugs and pharmaceutically acceptable esters; enantiomers and/or diastereoisomers of the compounds separated in their individual forms and/or in the forms of racemic or non-racemic mixtures with enantiomeric excess in any proportion.

EXAMPLES

The following examples described in detail illustrate the invention without, however, limiting its scope of protection, and that various modifications, in light of the same, will be suggestive to specialists in the art. Such equivalent achievements should be included within the scope and reach of the accompanying claims.

Example 1

Preparation of the Compound of Formula II Referred to as 3-(benzo[d][1,3]dioxol-5yl)-7-(2-hydroxyethyl)-1-(1H-indol-3-yl)-6,7-dihydro-3H-oxazolo[3,4-a]pyrazine-5,8-dione (BL-230)

In a 500 mL flask equipped with a mechanical stirrer, an addition funnel and a drying tube containing CaCl$_2$, were added the compound (a) (10.20 g, 28.0 mmol) and a solution of dry pyridine (11.3 ml) to 102 mL of dry tetrahydrofuran (THF), which was stirred for 30 minutes. To this suspension was added slowly, over about 2 hours, a solution of Chloroacetyl chloride (2.9 mL, 36.4 mmol) (reagent 2) in 30 mL of dry THF. After the addition, the reaction mixture was reacted for 4 hours at room temperature, resulting in the formation of the intermediate (b). At the end of this period, ethanol (42 mL) and the compound (c) known as 2-aminoethanol (39.3 g, 644.0 mmol) were added to the medium and the mixture was stirred for a period of 16 hours. At the end of this time were added to the medium 250 ml of ethanol and 100 ml of water. The system was subjected to vacuum distillation and excess solvent was removed until product precipitation. The flask was cooled to room temperature, and then cooled at a temperature between 0 and 5° C. The cooled system was maintained under stirring for 2 hours at a temperature between 0 and 5° C. The resulting suspension was vacuum filtered and the precipitate was washed with 100 ml of ethanol. The solid was placed in a 250 mL flask and 60 ml of ethanol was added and the mixture was stirred for 30 minutes. After this period, the solid was filtered and dried under a vacuum resulting in the formation of the product of formula (II) according to the scheme [1] below.

Scheme [1]: Synthesis of compound 3-(benzo[d][1,3]dioxol-5yl)-7-(2-hydroxyethyl)-1-(1H-indol-3-yl)-6,7-dihydro-3H-oxazolo[3,4-a]pyrazine-5,8-dione (BL-230)

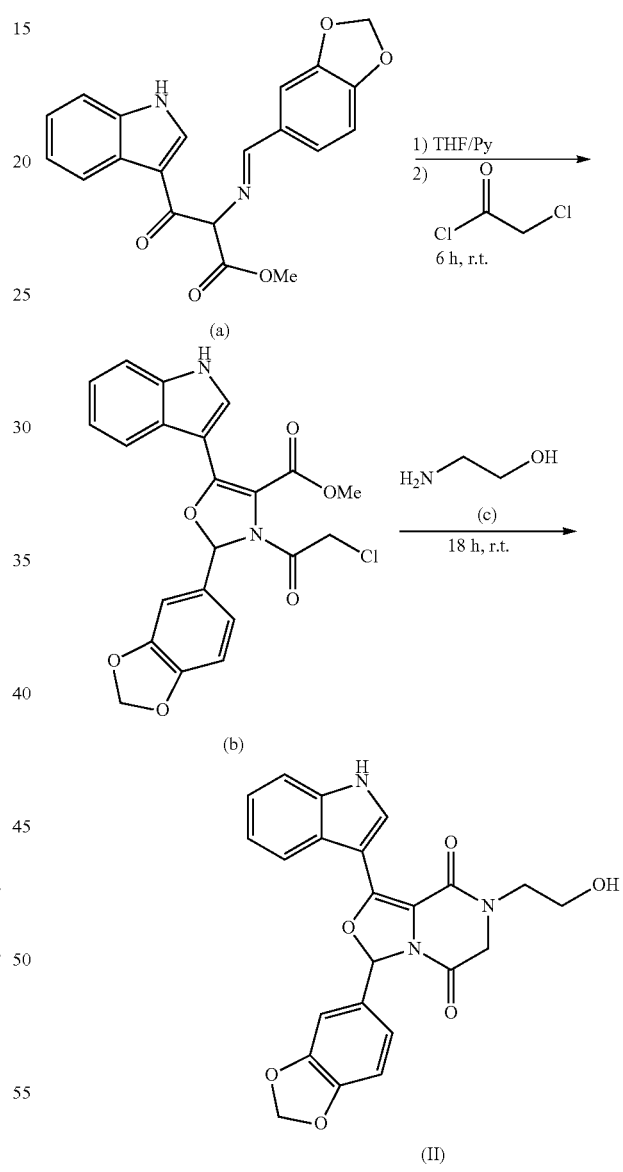

The compound obtained by this process has the IUPAC name 3-(benzo[d][1,3]dioxol-5yl)-7-(2-hydroxyethyl)-1-(1H-indol-3-yl)-6,7-dihydro-3H-oxazolo[3,4-a]pyrazine-5,8-dione (BL-230), chemical structure described by formula (II):

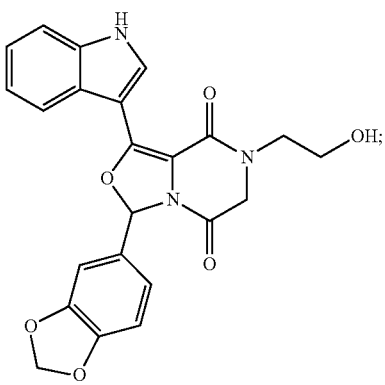

Figure 2:
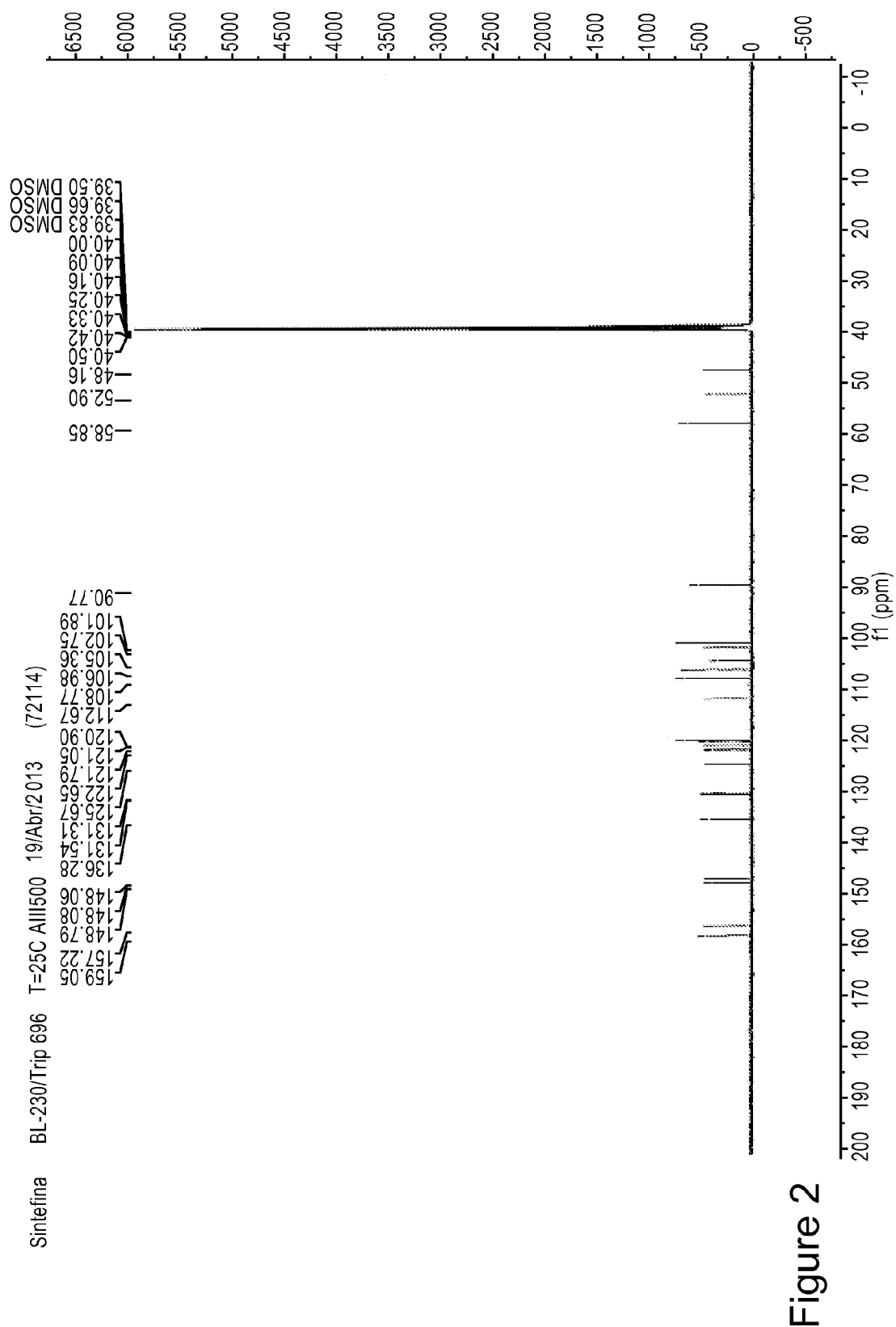
FIG. 2 shows the $^{13}$C NMR spectrum for the characterization of the compound obtained in Example 1 (BL-230).
Figure 3:
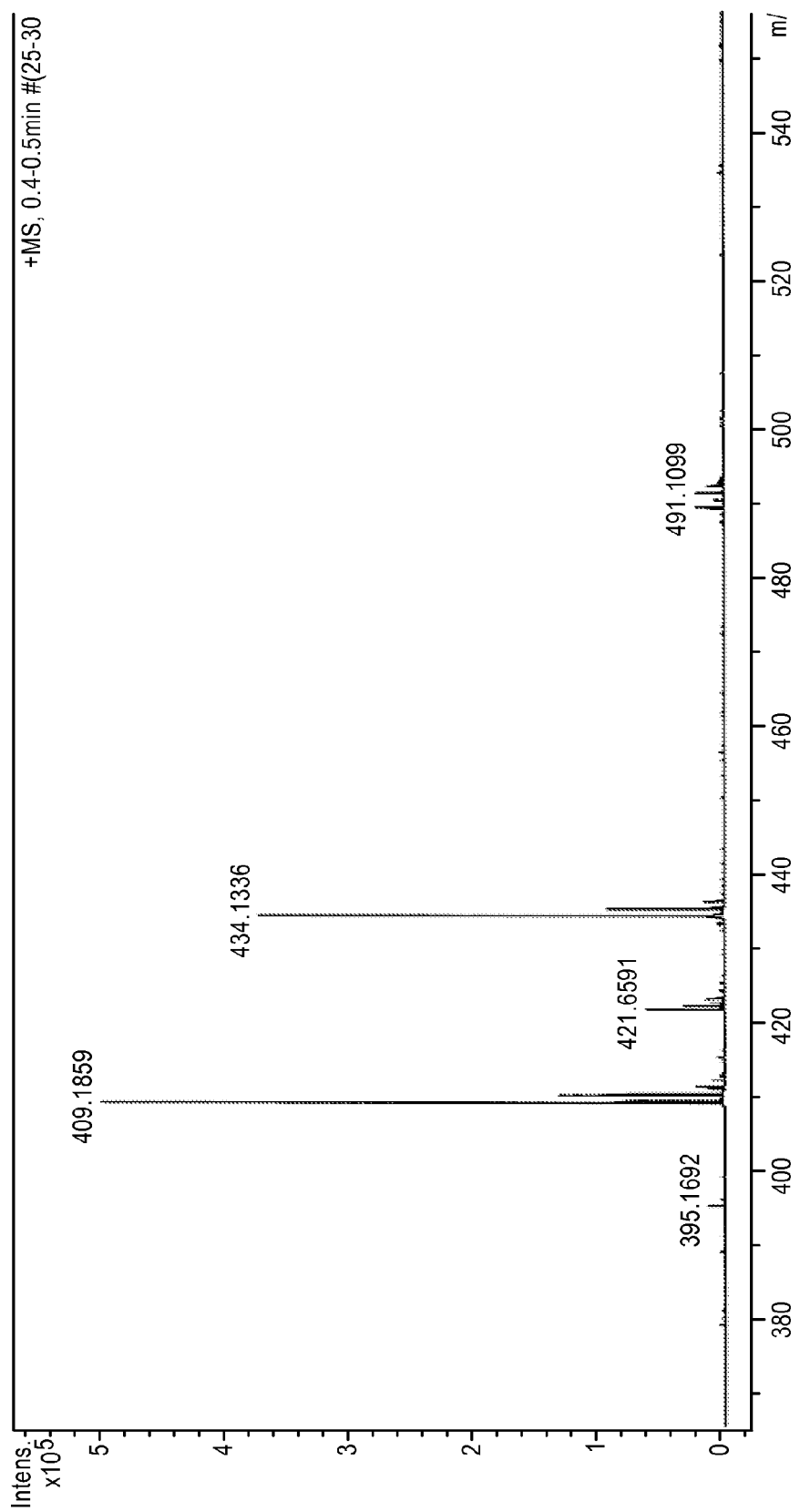
FIG. 3 shows the HRMS spectrum for the characterization of the compound obtained in Example 1 (BL-230).

(II)

and has the following characteristics: molecular formula: $C_{23}H_{19}N_3O_6$; yellow solid; Melting point 254-258° C., $^1H$ NMR (500 MHz, $(CD_3)_2SO$): δ 11.87 (1s, 1H), 8.96 (is, 1H), 7.85 (d, J=10.0 Hz, 1H), 7.47 (d, J=10.0 Hz, 1H), 7.18 to 7.05 (m, 5H), 6.98 (d, J=10.0 Hz, 1H), 6.05 (s, 2H), 4.84-4.32 (m, 1H); 4.28 (dd, J=30.0 Hz, J=15.0 Hz, 2H), 3.65-3.61 (m, 2H), 3.50 to 3.45 (m, 2H) (FIG. 1); $^{13}C$ NMR (125 MHz, $(CD_3)_2SO$): δ 159.1, 157.2, 148.8, 148.1, 148.0, 136.3, 131.5, 131.3, 125.7, 122.7, 121.8, 121.1, 120.9, 112.7, 108.8, 107.0, 105.4, 102.8, 101.9, 90.8, 58.9, 52.9, 48.2 (FIG. 2); HRMS (EI) m/z calculated for $C_{23}H_{19}N_3O_6$: [433.1274]$^+$. found: 434.1336 [M+H]$^+$ (FIG. 3).

Example 2

Preparation of the Compound of Formula (III) Referred to as 3-(benzo[d][1,3]dioxol-5yl)-7-((S)1-hydroxypropan-2yl)-1-(1H-indol-3-yl)-6,7-dihydro-3H-oxazolo[3,4-a]pyrazine-5,8-dione (BL-236)

In a 500 mL flask equipped with a mechanical stirrer, an addition funnel and a drying tube containing $CaCl_2$, were added the compound (a) (10.20 g, 28.0 mmol) and a solution of dry pyridine (11.3 ml) to 102 mL of dry tetrahydrofuran (THF), which was stirred for 30 minutes. To this suspension was added slowly, over about 2 hours, a solution of Chloroacetyl chloride (2.9 mL, 36.4 mmol) (reagent 2) in 30 mL of dry THF. After the addition, the reaction mixture was reacted for 4 hours at room temperature, resulting in the formation of the intermediate (b). At the end of this period, ethanol (42 mL) and the compound (d) referred to as (S)-2-aminopropan-1-ol (48.4 g, 644.0 mmol) were added to the medium and the mixture was stirred for a period of 16 hours. At the end of this time, 250 ml of ethanol and 100 ml of water were added to the medium. The system was subjected to vacuum distillation and the excess solvent removed until product precipitation. The flask was cooled to room temperature, and then cooled at a temperature between 0 and 5° C. The cooled system was maintained under stirring for 2 hours at temperature between 0 and 5° C. The resulting suspension was vacuum filtered and the precipitate was washed with 100 ml of ethanol. The solid was placed in a 250 mL flask, 60 ml of ethanol was added and the mixture was stirred for 30 minutes. After this period, the solid was filtered and dried under a vacuum resulting in the formation of the product of formula (III) according to the scheme [2] below.

Scheme [2]: Synthesis of Compound 3-(benzo[d][1,3]dioxol-5yl)-7-((S)1-hydroxypropan-2yl)-1-(1H-indol-3-yl)-6,7-dihydro-3H-oxazolo[3,4-a]pyrazine-5,8-dione (BL-236)

[2]

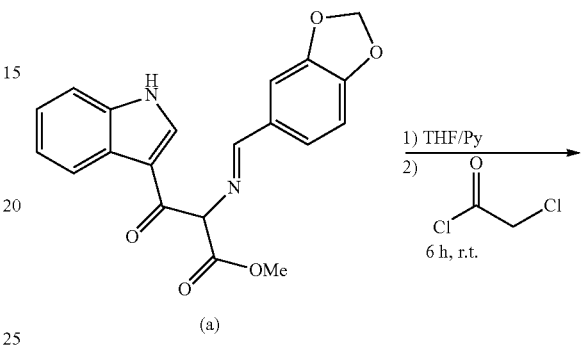

(a)

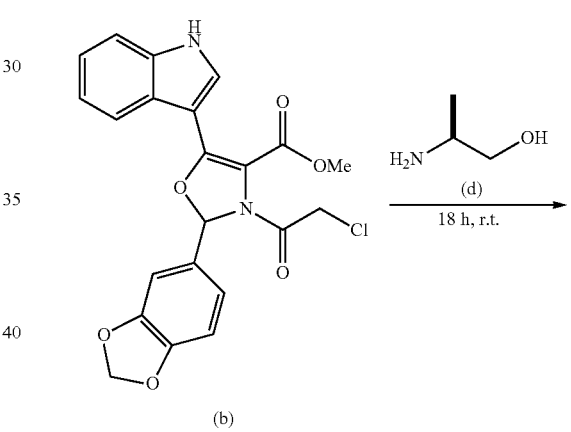

(b)

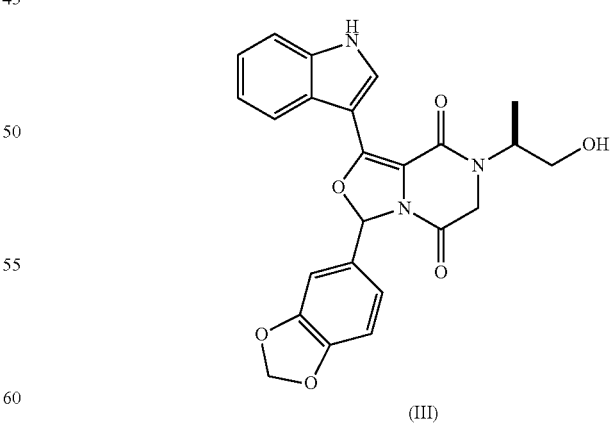

(III)

The compound obtained by this process has the IUPAC name 3-(benzo[d][1,3]dioxol-5yl)-7-((S)1-hydroxypropan-2yl)-1-(1H-indol-3-yl)-6,7-dihydro-3H-oxazolo[3,4-a]pyrazine-5,8-dione, (BL-236), chemical structure described by formula (III):

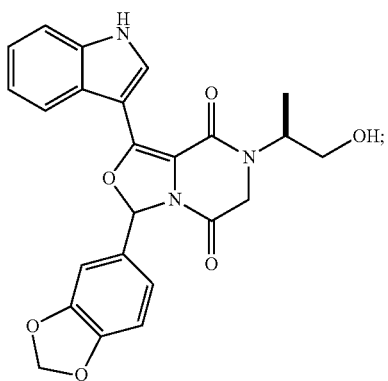

Figure 4:
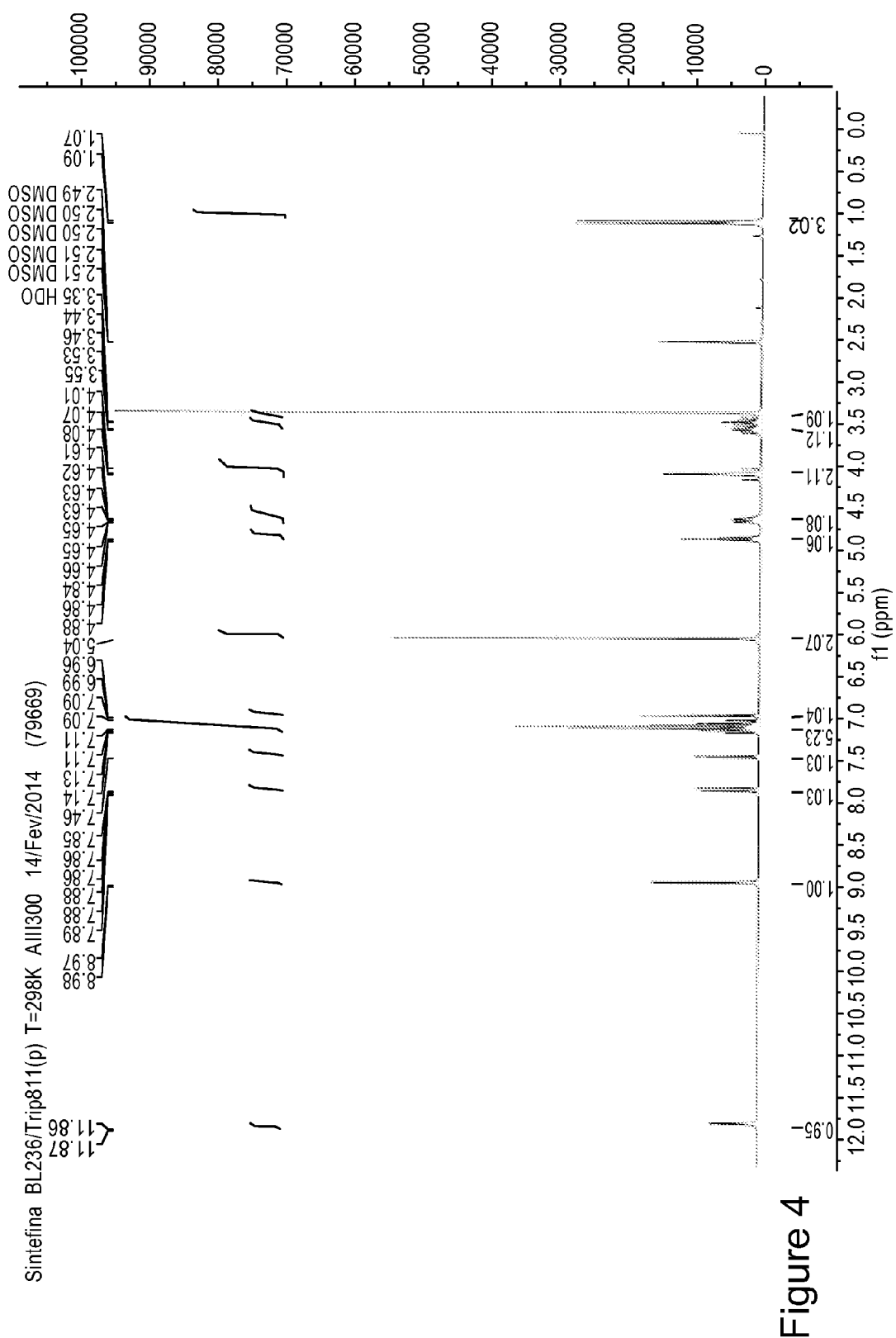
FIG. 4 shows the $^1$H NMR spectrum for the characterization of the compound obtained in Example 2 (BL-236).
Figure 5:
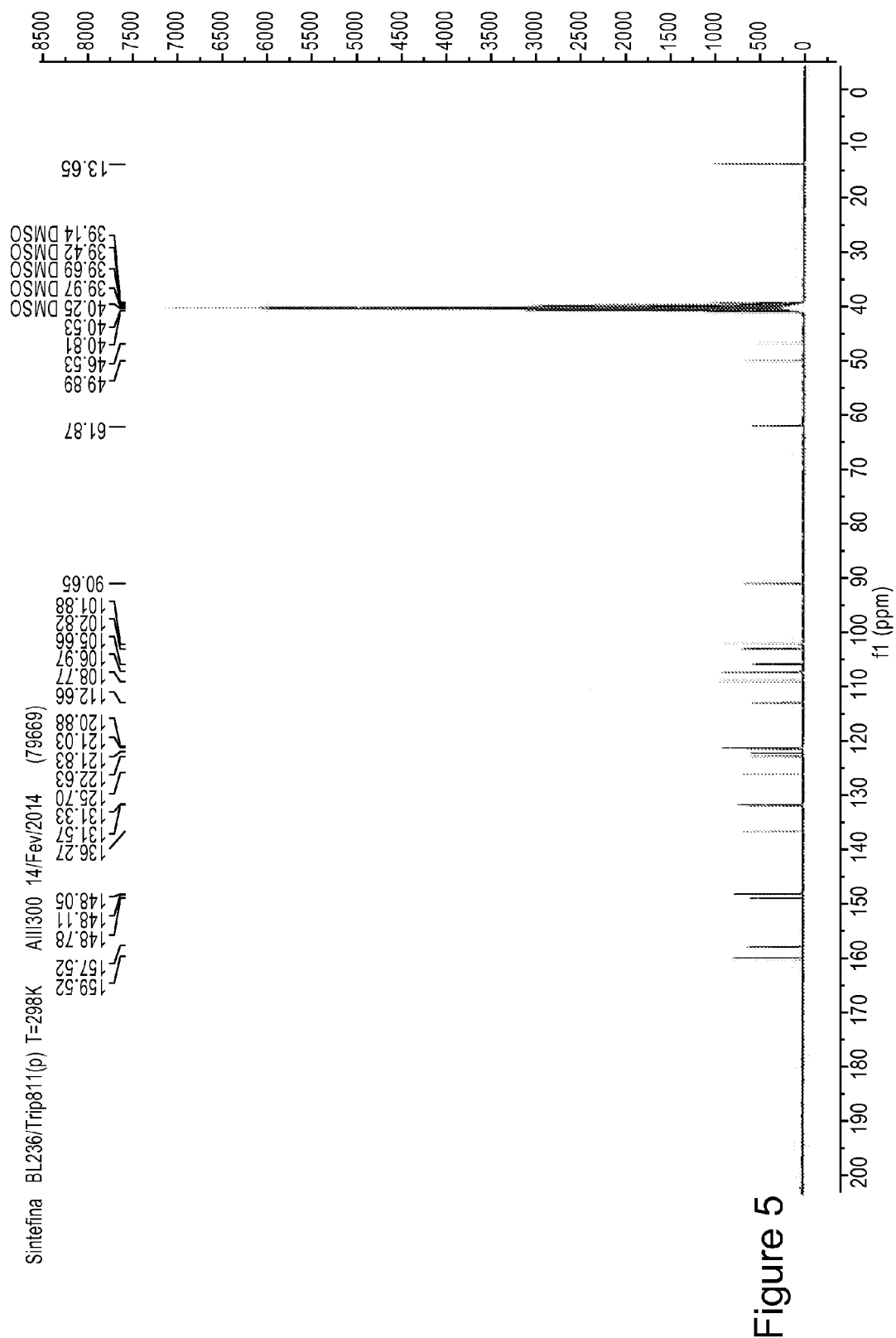
FIG. 5 shows the $^{13}$C NMR spectrum for the characterization of the compound obtained in Example 2 (BL-236).
Figure 6:
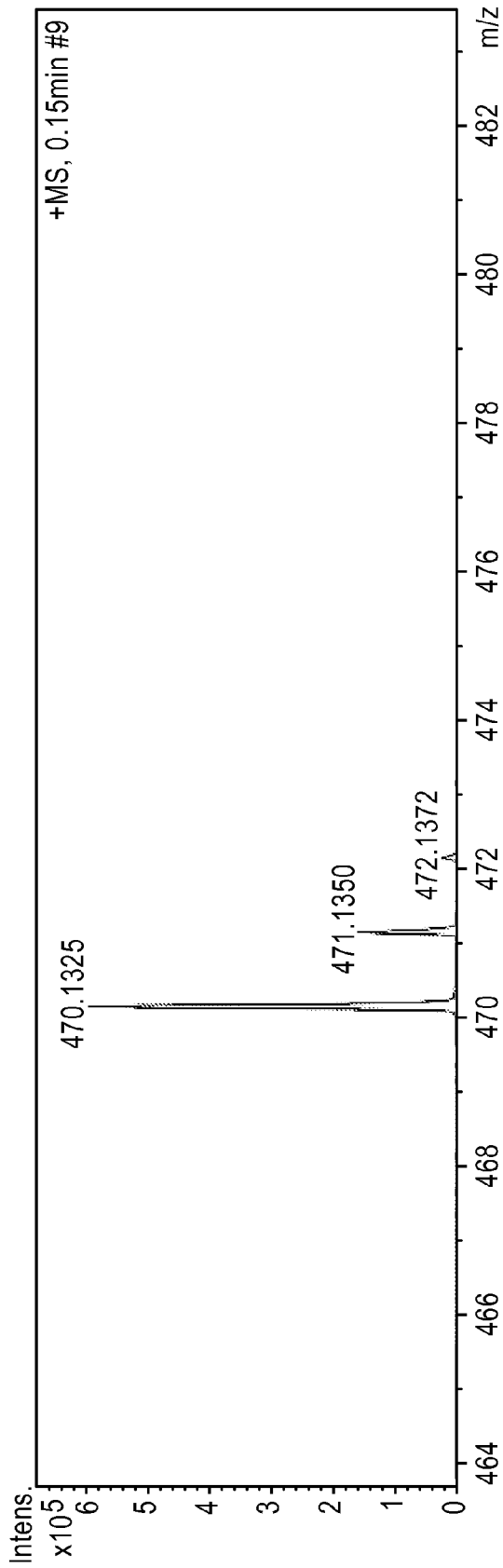
FIG. 6 shows the HRMS spectrum for the characterization of the compound obtained in Example 2 (BL-236).

(III)

and has the following characteristics: molecular formula: $C_{24}H_{21}N_3O_6$; yellow solid; Melting point 235-239° C., $^1$H NMR (300 MHz, $(CD_3)_2SO$): δ 11.87 (d, J=3.0 Hz, 1H), 8.98 (d, J=3.0 Hz, 1H), 7.87 (d, J=9.0 Hz, 1H), 7.47 (d, J=9.0 Hz, 1H), 7.14 to 7.06 (m, 5H), 6.98 (d, J=9.0 Hz, 1H), 6.4 (s, 2H), 4.85 (t, J=6.0 Hz, 1H), 4.67 to 4.60 (m, 1H), 4.07 (dd, J=21.0 Hz, J=18.0 Hz, 2H), 3.59 to 3.52 (m, 1H), 3.51 to 3.40 (m, 1H), 1.07 (d, J=6.0 Hz, 3H) (FIG. 4); $^{13}$C NMR, 75 MHz, $(CD_3)_2SO$, δ 159.5, 157.5, 148.8, 148.1, 148.0, 136.3, 131.6, 131.3, 125.7, 122.6, 121.8, 121.0, 120.9, 112.8, 108.8, 107.0, 105.7, 102.8, 101.9, 90.7, 61.9, 49.9, 46.5, 13.7 (FIG. 5); HRMS (EI) m/z calculated for $[C_{24}H_{21}N_3O_6]$+: 447.1430. found: 470.1325 $[M+Na]^+$ (FIG. 6).

Example 3

Evaluation of the Relaxing Effect of BL-230 and BL-236 Compounds in Isolated Rabbit's Corpus Cavernosum Tissue For this study, New Zealand White rabbits (2 to 3.5 kg) were used to obtain penile tissue which was excised and transferred to a chilled Krebs solution. For this study, we used cavernosum strips (CC) of the penile tissue of New Zealand White rabbits.

Record of Isometric Tension

The strips were mounted in 10 ml tissue incubation chambers containing Krebs solution at 37° C., pH occurring between 7.3 and 7.5; continuously bubbled with a mixture of 95% oxygen ($O_2$) and 5% carbon dioxide ($CO_2$). An initial tension of 10 mN were applied on the tissues, followed by a 60 minute stabilization period. Changes in tension (isometric force) were obtained using isometric transducers (ADInstruments, Australia) and recorded in a data acquisition system PowerLab 4/30 (Chart Software, version 7.3.7, ADInstruments, MA, USA for BL-230 and version 7.0 ADInstruments, MA for the BL-236).

Figure 7:
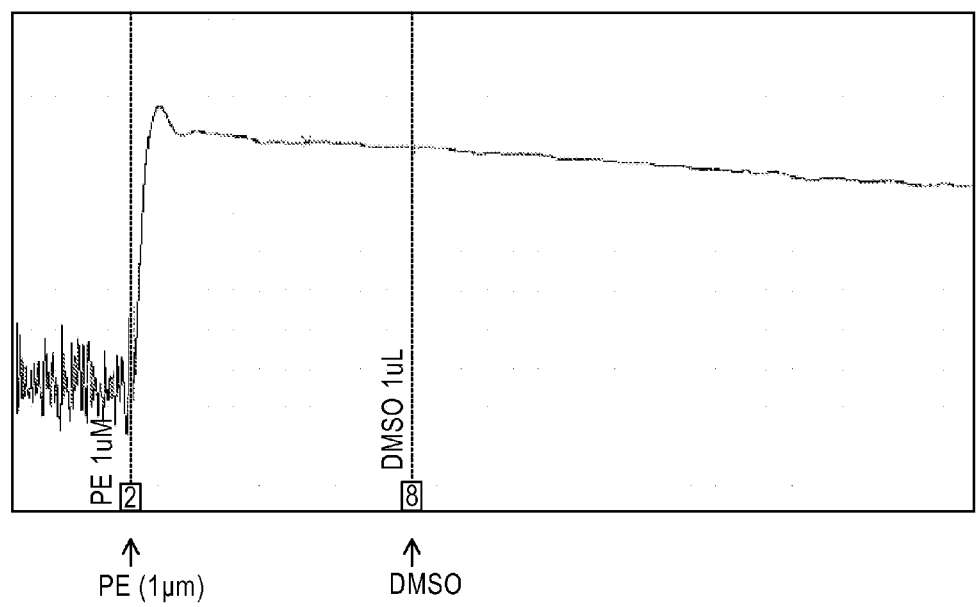
FIG. 7 shows a graph of the contraction induced by phenylephrine (PE) and the effect of DMSO (vehicle–negative control) in rabbit's corpus cavernosum.
Figure 8:
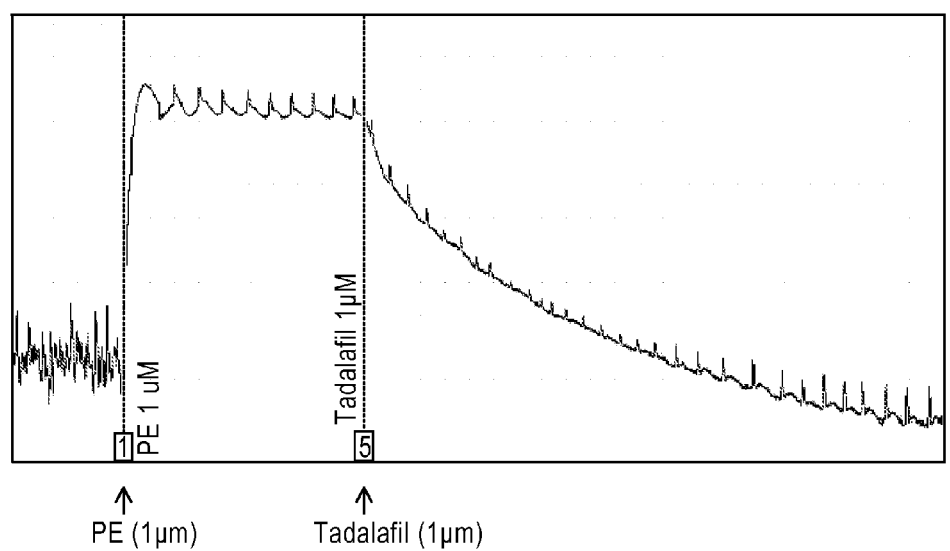
FIG. 8 shows a graph of the contraction induced by phenylephrine (PE) and the relaxant effect of tadalafil in rabbit's corpus cavernosum.
Figure 9:
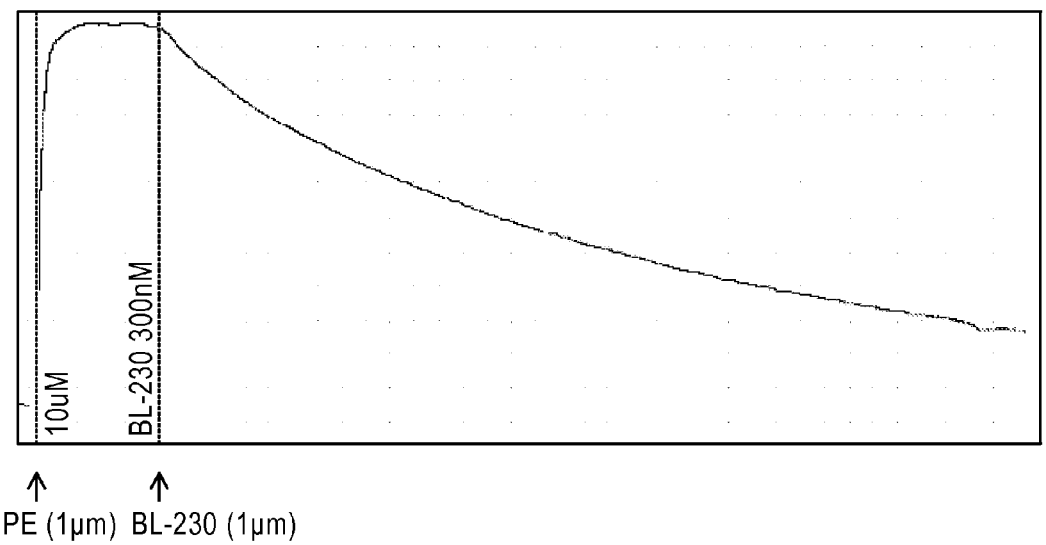
FIG. 9 shows a graph of the contraction induced by phenylephrine (PE) and the relaxant effect of the BL-230 compound in rabbit's corpus cavernosum.
Figure 10:
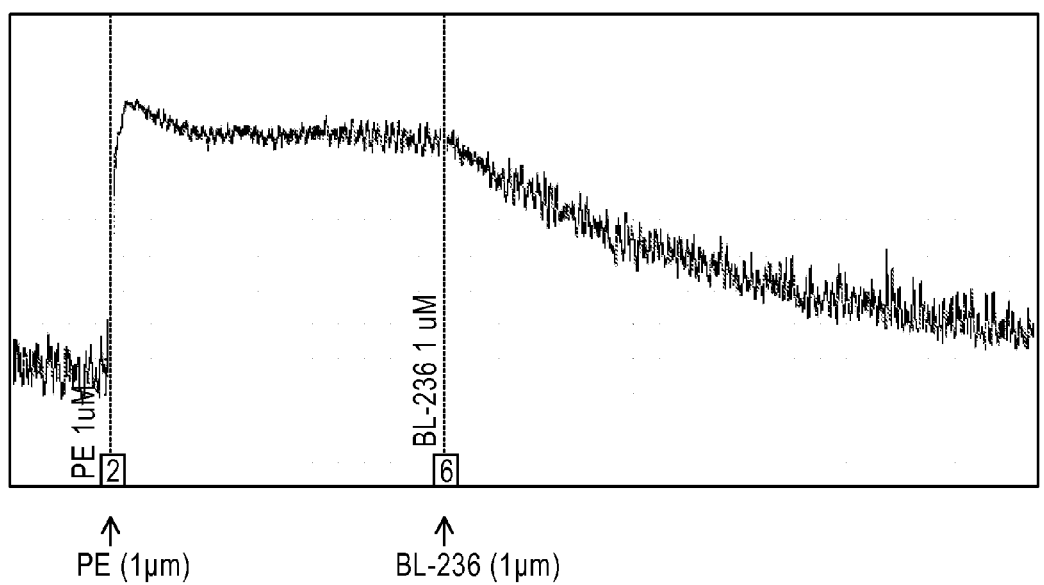
FIG. 10 shows a graph of the contraction induced by phenylephrine (PE) and the relaxant effect of the BL-236 compound in rabbit's corpus cavernosum.

Analyzing the data, one can observe that: (a) 1 μM of phenylephrine (PE) was able to induce sustained contraction in the rabbits' corpus cavernosum tissue, as can be seen in FIGS. 7 to 10; (b) the administration of dimethylsulfoxide (DMSO), carrier used to solubilize the compounds, did not induce tissue relaxation (FIG. 7); (C) the administration of 1 μM of tadalafil resulted in tissue relaxation (FIG. 8); (D) and the BL-230 and BL-236 compounds in a concentration of 1 μM produced tissue relaxation shape similar to that of tadalafil in the same concentration (FIGS. 9 and 10, respectively).

Figure 11:
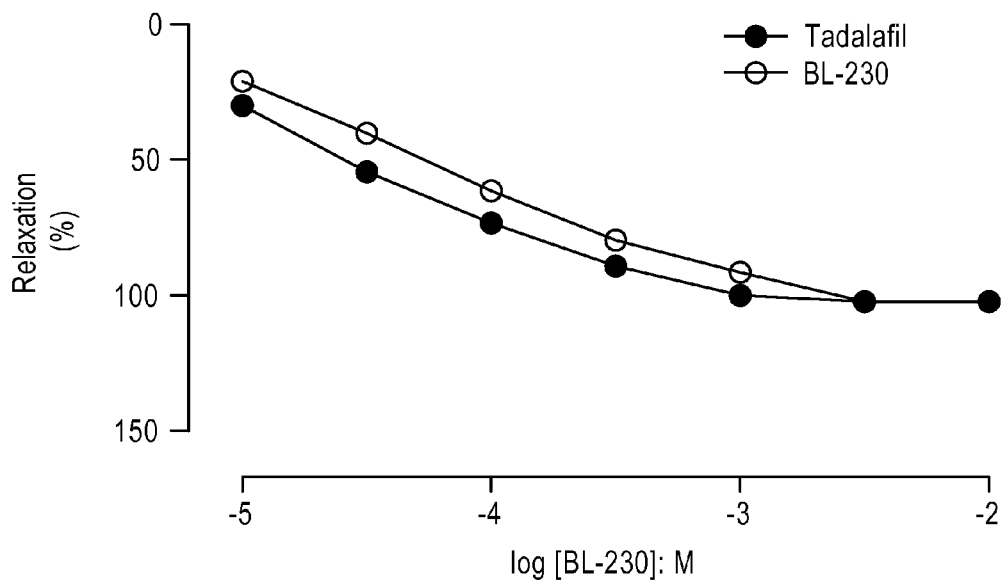
FIG. 11 shows a dose-response curve graph, with the percentage of relaxation in rabbit's corpus cavernosum after administration of the BL-230 compound and tadalafil.
Figure 12:
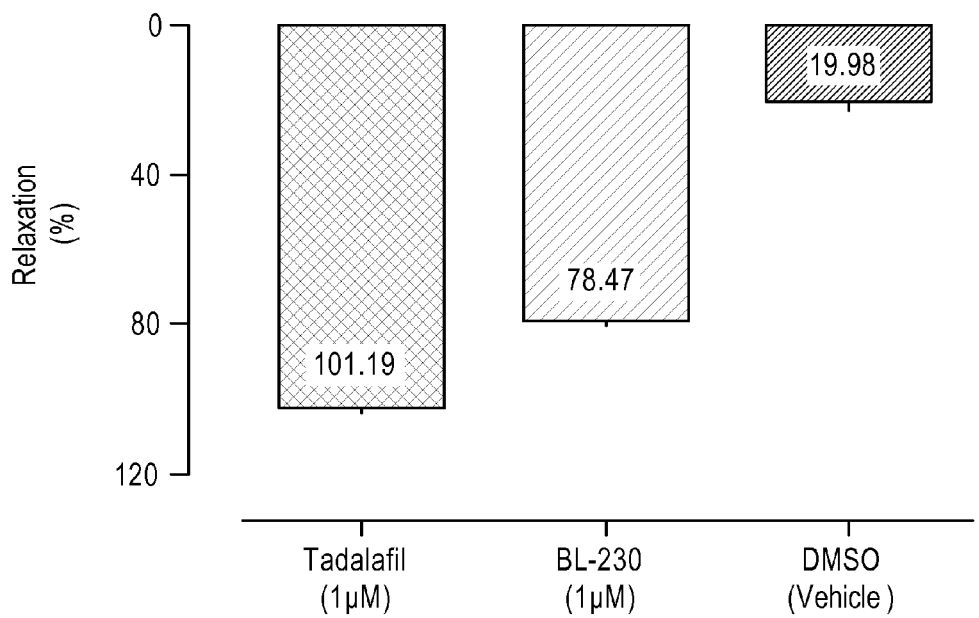
FIG. 12 shows a bar graph of the percentage of relaxation in rabbit's corpus cavernosum when BL-230, tadalafil and DMSO (vehicle) were administered.

Cumulative curve responses to the concentration of BL-230 compounds and tadalafil (0.001 to 10 μM) were obtained in the pre-contracted rabbit corpus cavernosum strips with 1 μM PE. As can be seen in FIG. 11, the BL-230 compound produced a dose-dependent relaxation similar to that observed for tadalafil (0.001 to 10 μM) caused by the phenylephrine contraction. Additionally, FIGS. 12 and 13 also illustrate the relaxation observed with the compounds BL-230, BL-236 and tadalafil, where it is possible to observe (FIGS. 12 and 13), that BL-230 was able to induce 78.47% relaxation of the rabbit corpus cavernosum, while BL-236 induced 93.05%, and tadalafil induced relaxation in the corpus cavernosum of around 100%. On the other hand, DMSO showed insignificant relaxation of about 20.

The results show that the BL-230 and BL-236 compounds produce relaxation in the corpus cavernosum tissue of rabbits.

Example 4

In Vitro Pre-Clinical Study to Evaluate the Inhibition Profile of Phosphodiesterases (PDE) for BL-230 Compounds of Formula (II) and BL-236 of Formula (III)

These studies were conducted to evaluate the inhibition profile of 13 types of human phosphodiesterases (PDE), for the BL-230 and BL-236 compounds. More specifically, the inhibition profile of $PDE1B$, $PDE2A_1$, $PDE3A$, $PDE3B$, $PDE4A_{1,4}$, $PDE4B_1$, $PDE4D_2$, $PDE5$, $PDE6$, $PDE7A$, $PDE8A_1$, $PDE10A_2$ and $PDE11A_4$. For these studies, enzymatic trials were performed which were already known and standardized by the prior art.

4.1: Activity of the effects of BL-230 and BL-236 compounds on the activity of PDE1B enzyme.

The effects of BL-230 and BL-236 compounds on the activity of PDE1B human enzymes were quantified by measuring the production of guanosine 5'-monophosphate (5'GMP) from cyclic guanosine monophosphate (cGMP), using human recombinant enzyme expressed in Sf9 cells, and the detection method was by using HTRF® (Homogeneous Time Resolved Fluorescence Technology).

The test compound, the reference compound or the water (control) were mixed with 0.07 U from the enzyme PDE1B in a buffer containing 44.4 mM Tris-hydroxymethyl aminomethane hydrochloride (Tris-HCl), 5.28 mM magnesium chloride ($MgCl_2$), 0.88 mM calcium chloride ($CaCl_2$), 2.64 mM dithiothreitol (DTT) and 0.198 U of calmodulin and 0.044% polysorbate 20 (Tween® 20) (pH 7.8). Then, the reaction was initiated by the addition of 240 nM cGMP substrate, and the mixture was incubated for 30 minutes at room temperature. For basal control measurements, the enzyme was omitted from the reaction mixture. The fluorescence acceptor (Dye2 labeled cGMP) and fluorescence donor (anti-cGMP antibody labeled with europium cryptate) were added in the presence of 1 mM 3-isobutyl-1-methylxanthine (IBMX). After 60 minutes, the transfer of fluorescence corresponding to the amount of residual cGMP was measured at λex=337 nm, λem=620 nm and λem=665 nm using a microplate reader (RubyStar, BMG). The enzyme activity was determined by the signal division measured at 665 nm, by the measured signal at 620 nm (right). The results were expressed as a inhibition percentage of the control enzyme activity. The standard inhibitory reference compound calmidazolium was used, which was tested in each experiment at several concentrations to obtain an inhibition curve from which its $IC_{50}$ value was calculated.

For this trial, the researchers used as a basis the teachings described by Bender (BENDER, A T and Beavo, J A (2006). *Cyclic nucleotide phosphodiesterases: Molecular regulation to clinical use*, Pharmacol. Rev., 58: 488).

According to the results, we observed (FIGS. 14 and 15) that the BL-230 and BL-236 compounds, respectively, did not inhibit the activity of the PDE1B enzymes.

4.2: Activity of the effects of the BL-230 and BL-236 compounds on the activity of the enzymes $PDE2A_1$, PDE3A, $PDE4A_{1A}$, $PDE4B_1$, PDE7A, $PDE8A_1$, $PDE10A_2$ and $PDE11A_4$.

The effects of the BL-230 and BL-236 compounds on the activity of the human enzymes $PDE2A_1$, PDE3A, $PDE4A_{1A}$, $PDE4B_1$, PDE7A, $PDE8A_1$, and $PDE10A_2$ and $PDE11A_4$ were quantified by measuring the production of adenosine 5'-monophosphate (5'AMP) from cyclic adenosine monophosphate (cAMP), with human recombinant enzyme expressed in Sf9 cells and the detection method was by using HTRF®.

The test compound, the reference compound or water (control) were mixed with the enzyme (the enzymes and their amounts used are described in Table 1) in a buffer containing 44.4 mM Tris-HCl, 5.28 mM $MgCl_2$, 2.64 mM DTT and 0.044% Tween® 20 (pH 7.8). Then, the reaction was initiated by the addition of 40 nM of cAMP substrate and the mixture was incubated for 30 minutes at room temperature. For basal control measurements, the enzyme was omitted from the reaction mixture. The fluorescence acceptor (Dye2 labeled cAMP) and fluorescence donor (anti-cAMP antibody labeled with europium cryptate) were added in the presence of 1 mM IBMX. After 60 minutes, the fluorescence corresponding to the amount of transfer residual cAMP was measured at $\lambda ex=337$ nm, $\lambda em=620$ nm and $\lambda em=665$ nm using a microplate reader (RubyStar, BMG). The enzyme activity was determined by the signal division measured at 665 nm, by the measured signal at 620 nm (right). The results were expressed as a inhibition percentage of the control enzyme activity. The standard inhibitory reference compounds used for each of the enzymes used are described in Table 1, which was tested in each experiment at several concentrations to obtain an inhibition curve from which its $IC_{50}$ value was calculated.

For this trial, the researchers used as a basis the teachings described by: Bender (BENDER, A T and Beavo, J A (2006), Cyclic nucleotide phosphodiesterases: Molecular regulation to clinical use, Pharmacol. Rev., 58: 488 [$PDE3A_1$ and PDE2A]); Saldou (SALDOU, N., et al. (1998) Comparison of recombinant human PDE4 isoforms: interaction with substrate and inhibitors, Cell Signal., 10: 427. [$PDE4A_{1A}$ and $PDE4_{B1}$]; Smith (SMITH, S J, et al. (2004) Discovery of BRL 50481 [N,N-dimethylsulfonamido)-4-methyl-nitrobenzene], a selective inhibitor of phosphodiesterase 7: in vitro studies in human monocytes, lung macrophages, and CD8+T-lymphocytes, Mol Pharm., 66: 1679. [PDE7A]); Fisher (FISHER, D A, et al. (1998), Isolation and characterization of PDE8A, a novel human cAMP-specific phosphodiesterase Biochem, 246: 570. [$PDE8A_1$]); Soderling (SODERLING S H, et al. (1999), Isolation and characterization of a dual-substrate phosphodiesterase gene family: PDE10A, Proc. Natl. Acad. Sci. USA, 96:7071 [$PDE10A_2$]); and Fawcett (FAWCET L., et al. (2000), Molecular cloning and characterization of a distinct human phosphodiesterase gene family: PDE11A, Proc. Natl. Acad. Sci., 97: 3702. [$PDE11A_4$].

TABLE 1

List of enzymes and their respective PDE inhibitor reference standard compounds.

| Enzymes(s) | Quantitiy(s) | Standard Inhibitor Reference Compound |
|---|---|---|
| $PDE2A_1$ | 8 U of $PDE2A_1$ | EHNA |
| PDE3A | 1 U of PDE3A | Milrinone |
| $PDE4A_{1A}$ | 5 U of $PDE4A_{1A}$ | Rolipram |
| $PDE4B_1$ | 4.8 U of $PDE4B_1$ | Rolipram |
| PDE7A | 0.1 U of PDE7A | BRL 50481 |
| $PDE8A_1$ | 1.2 U of $PDE8A_1$ | Dipyridamole |
| $PDE10A_2$ | 0.25 U of $PDE10A_2$ | Papaverine |
| $PDE11A_4$ | 1 U of $PDE11A_4$ | Papaverine |

According to the obtained results, we observed (FIGS. 14 and 15) that the BL230 and BL-236 compounds, respectively, did not inhibit the activity of the enzymes $PDE2A_1$, PDE3A, $PDE4A_{1A}$, $PDE4B_1$, PDE7A and $PDE8A_1$. While the compounds BL230 and BL-236 inhibited 75% and 80%, respectively, the enzyme activity of $PDE11A_4$. And additionally, it's possible observe that the BL-230 compound was able to inhibit the enzyme activity of $PDE10A_2$ by 35%.

4.3: Activity of the effects of the BL-230 and BL-236 compounds on the activity of the PDE3B enzyme.

The effects of compounds BL-230 and BL-236 on human PDE3B enzyme activity was quantified by measuring the production of 5'AMP from CAMP using human recombinant enzyme expressed in Sf9 cells and the detection method was by using HTRF®.

The test compound, the reference compound or water (control) were mixed with 0.7 U of the enzyme PDE3B in a buffer containing 50 mM Tris-HCl, 6 mM $MgCl_2$, 3 mM DTT and 0.05% Tween® 20 (pH 7.8). Then, the reaction was initiated by addition of 40 nM of cAMP substrate and the mixture was incubated for 30 minutes at 22° C. For basal control measurements, the enzyme was omitted from the reaction mixture. The fluorescence acceptor (Dye2 labeled cAMP) and fluorescence donor (anti-cAMP antibody labeled with europium cryptate) were added in the presence of 1 mM IBMX. After 60 minutes, the transfer of fluorescence corresponding to the amount of residual cAMP was measured at $\lambda ex=337$ nm, $\lambda em=620$ nm and $\lambda em=665$ nm using a microplate reader (RubyStar, BMG). The enzyme activity was determined by the signal division measured at 665 nm, by the signal measured at 620 nm (right). The results were expressed as an inhibition percentage of the control enzyme activity. The standard inhibitory reference compound milrinone was used, which was tested in each experiment at several concentrations to obtain an inhibition curve from which its $IC_{50}$ value was calculated.

For this trial, the researchers used as a basis the teachings described by Bender (BENDER, A. T. and Beavo, J. A. (2006), *Cyclic nucleotide phosphodiesterases: Molecular regulation to clinical use*, Pharmacol. Rev., 58: 488)

According to the obtained results, we observed (FIGS. 14 and 15) that the BL-230 and BL-236 compounds, respectively, did not inhibit the activity of the PDE3B enzymes.

4.4: Activity of the effects of the BL-230 and BL-236 compounds on PDE4D2 enzyme activity.

The effects of the BL-230 and BL-236 compounds on the activity of the human $PDE4D_2$ enzyme were quantified by measuring the production from 5' AMP cAMP using a human recombinant enzyme expressed in Sf9 cells and the method of detection used was the HTRF®.

The test compound, the reference compound or the water (control) were mixed with 0.75 U of $PDE4D_2$ in a saline buffer solution balanced with Hanks (HBSS) (Invitrogen) supplemented, and 1.5 mM $MgCl_2$, 0.1% bovine serum albumin (BSA). Then, the reaction was initiated by addition of 40 nM of cAMP substrate and the mixture is incubated for 15 minutes at 37° C. For basal control measurements, the enzyme was omitted from the reaction mixture. The fluorescence acceptor (Dye2 labeled cAMP) and fluorescence donor (anti-cAMP antibody labeled with europium cryptate) are added in the presence of 1 mM IBMX. After 60 minutes at room temperature, the fluorescence corresponding to the amount of transfer residual cAMP was measured at λex=337 nm, λem=620 nm and λem=665 nm using a microplate reader (Envision, Perkin Elmer). The enzyme activity was determined by the signal division measured at 665 nm, by the measured signal at 620 nm (ratio). The results were expressed as an inhibition percentage of the control enzyme activity. The standard inhibitory reference compound rolipram was used, which was tested in each experiment at several concentrations to obtain an inhibition curve from which its $IC_{50}$ value was calculated.

For this trial, the researchers used as a basis the teachings described by Saldou (SALDOU, N., et al. (1998) Comparison of recombinant human PDE4 isoforms: interaction with substrate and inhibitors, Cell Signal., 10: 427).

According to the obtained results, it can be seen (Figures and 15) that the compound BL-230 inhibited 55% of the enzyme activity of $PDE4D_2$, while the BL-236 compound showed no inhibitory effect on this enzyme.

4.5: Activity of the effects of the BL-230 and BL-236 compounds on the activity of PDE5 enzymes.

The effects of compounds BL-230 and BL-236 on human PDE5 enzyme activity was quantified by measuring the production of 5'GMP from cGMP using an enzyme isolated from Cerep human platelets and the utilized detection method was scintillation proximity assay (SPA).

The test compound, the reference compound or water (control) were added to a buffer containing 40 mM Tris-HCl (pH 7.8), 3 mM $MgCl_2$, 1.4 mM DTT, 0.21% BSA, 200 mM ammonium chloride ($NH_4Cl$), 1 μM cGMP and 0.1 μCi of [$^3H$]cGMP. Then the reaction was started by adding the enzyme (final amount depending on the efficiency of the isolation) and the mixture was incubated for 60 minutes at 22° C. For basal control measurements, the enzyme was omitted from the reaction mixture. Following this, the SPA incubation beads were added. After 20 min at 22° C. under agitation, the amount of [$^3H$] 5'GMP was quantified with a scintillation counter (Topcount, Packard). The results were expressed as an inhibition percentage of the control enzyme activity. The standard inhibitory reference compound dipyridamole was used, which was tested in each experiment at several concentrations to obtain an inhibition curve from which its $IC_{50}$ value was calculated.

For this trial, the researchers used as a basis the teachings described by Weishaar, (Weishaar, R. E., et al. (1986), *Multiple molecular forms of cyclic nucleotide phosphodiesterase in cardiac and smooth muscle and platelets* in Biochem. Pharmacol., 35:787).

Figure 15:
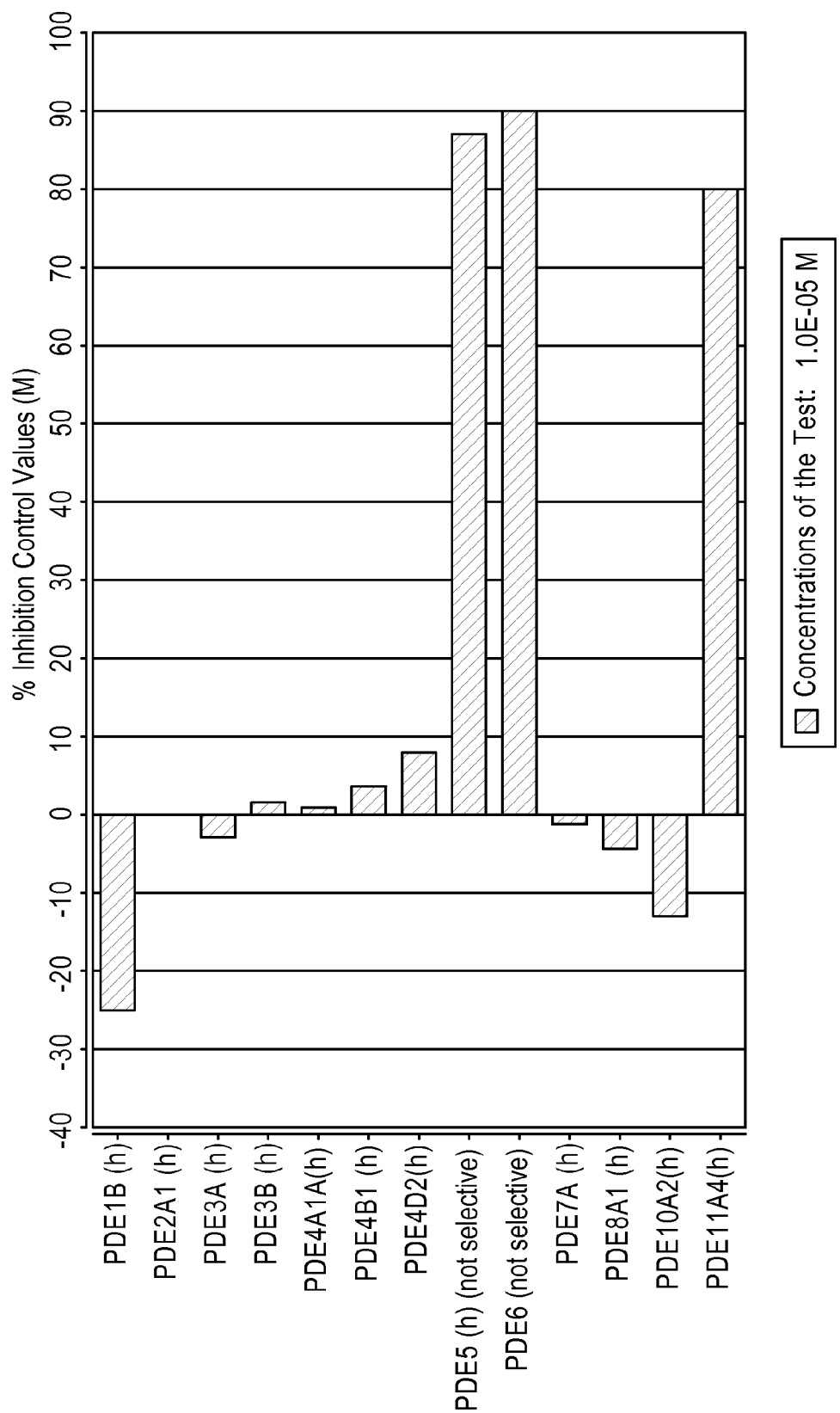
FIG. 15 shows the percentage of phosphodiesterase enzyme inhibition observed in the presence of the BL-236 compound.

According to the obtained results, the researchers found that the BL-230 and BL-236 compounds are potent inhibitors of PDE5, and that BL-230 showed 90% inhibition and BL-236 showed 86% inhibition (FIGS. 14 and 15 respectively).

4.6: Activity of the effects of the BL-230 and BL-236 compounds on the activity of PDE6 enzyme.

The effects of compounds BL-230 and BL-236 on PDE6 human enzyme activity were quantified by measuring the production of 5'GMP from cGMP, using an enzyme isolated from Cerep bovine retina of and the detection method used was scintillation proximity assay (SPA).

The test compound, the reference compound or water (control) were added to a buffer containing 40 mM Tris-HCl (pH 7.8), 3 mM $MgCl_2$, 1.4 mM DTT, 0.21% BSA, 200 mM $NH_4Cl$, 2 uM cGMP and 0.05 μCi of [$^3H$] cGMP. Then the reaction was started by adding the enzyme (final amount depending on the efficiency of the isolation) and the mixture was incubated for 60 minutes at 22° C. For basal control measurements, the enzyme was omitted from the reaction mixture. Following this, the SPA incubation beads were added. After 20 minutes at 22° C. under agitation, the amount of [$^3H$] 5'GMP was quantified with a scintillation counter (Topcount, Packard). The results were expressed as an inhibition percentage of the control enzyme activity. The standard inhibitory reference compound zaprinast was used, which was tested in each experiment at several concentrations to obtain an inhibition curve from which its $IC_{50}$ value was calculated.

For this trial, the researchers used as a basis the teachings described by Ballard (Ballard, A. S., et al. (1998) *Effects of sildenafil on the relaxation of human corpus cavernosum tissue in vitro and on the Activities of cyclic nucleotide phosphodiesterase isozymes*, J. Urol., 159. 2164).

According to the obtained results, the researchers found that the BL-230 and BL-236 compounds are potent inhibitors of PDE6, and that BL-230 showed 85% inhibition and BL-236 showed 90% inhibition (FIGS. 14 and 15 respectively).

Regardless of the tests used, the results showing inhibition (or stimulation) above 50% are indicative of a strong effect. The results show that inhibition (or stimulation) between 25% and 50% is indicative of low or moderate effect. The results of inhibition (or stimulation) lower than 25% are not considered significant, and mainly, are assigned to the signal variability around the control.

The invention claimed is:

1. A compound of formula (I)

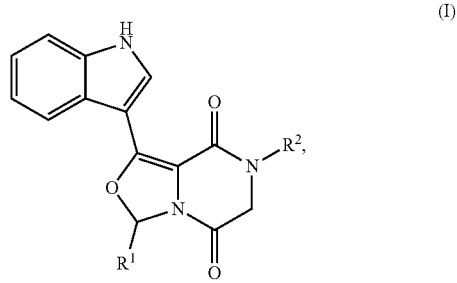

where:

$R^1$ is benzo[d][1,3]dioxolyl;

$R^2$ is $CH_2(CH_2)_nR^3$ or $CHR^6CH_2OH$;

$R^3$ is OH;

$R^6$ is $CH_3$; and n is 1;

or a pharmaceutically acceptable salt or stereoisomer thereof.

2. The compound according to claim 1, represented by formula (II):

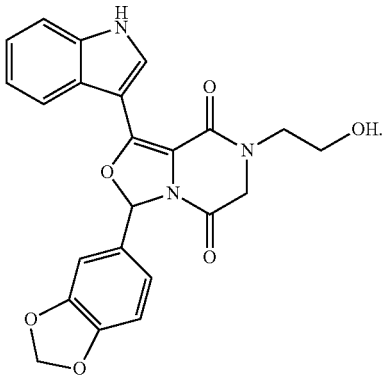

(II)

3. The compound according to claim 1, represented by formula (III):

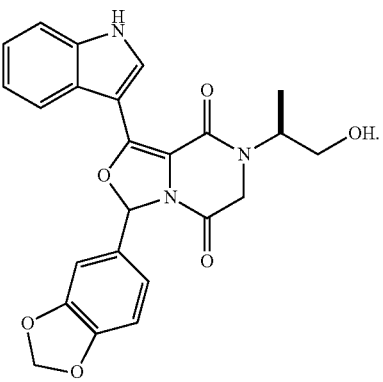

(III)

4. A pharmaceutical composition comprising a therapeutically effective amount of one or more compounds according to claim 1 and one or more pharmaceutically acceptable excipients.

5. The pharmaceutical composition according to claim 4, formulated for oral, topical, injectable, nasal and rectal administration.

6. The pharmaceutical composition according to claim 4, comprising as an active ingredient at least one compound selected from the group consisting of:
  (a) 3-(benzo[d][1,3]dioxol-5yl)-7-(2-hydroxyethyl)-1-(1H-indol-3-yl)-6,7-dihydro-3H-oxazolo[3,4-a]pyrazine-5,8-dione, or
  (b) 3-(benzo[d][1,3]dioxol-5yl)-7((S)1-hydroxypropan-2yl)-1-(1H-indol-3-yl)-6,7-dihydro-3H-oxazolo[3,4-a]pyrazine-5,8-dione, or
a pharmaceutically acceptable salt or stereoisomer thereof.

7. A method for inhibiting phosphodiesterase activity in a mammal, comprising administering to said mammal a therapeutically effective amount of a compound according to claim 1, or a pharmaceutically acceptable salt or stereoisomer thereof.

8. A process for the preparation of the compound of formula (II) according to claim 2, comprising the following steps:
  (i) reacting (E)-methyl 2-((benzo[d][1,3]dioxol-5-ylmethylene)amino)-3-(1H-indol-3-yl)-3-oxopropanoate with chloroacetyl chloride in a mixture of dry pyridine and tetrahydrofuran to provide methyl 2-(benzo[d][1,3]dioxol-5-yl)-3-(2-chloroacetyl)-5-(1H-indol-3-yl)-2,3-dihydrooxazole-4-carboxylate; and
  (ii) reacting methyl 2-(benzo[1,3]dioxol-5-yl)-3-(2-chloroacetyl)-5-(1H-indol-3-yl)-2,3-dihydrooxazole-4-carboxylate with 2-aminoethanol in ethanol to provide the compound of formula (II).

9. A process for the preparation of the compound of formula (III) according to claim 3, comprising the following steps:
  (i) reacting (E)-methyl 2-((benzo[d][1,3]dioxol-5-ylmethylene)amino)-3-(1H-indol-3-yl)-3-oxopropanoate with chloroacetyl chloride in dry pyridine\tetrahydrofuran to provide 2-(benzo[d][1,3]dioxol-5-yl)-3-(2-chloroacetyl)-5-(1H-indol-3-yl)-2,3-dihydrooxazole-4-carboxylate; and
  (ii) reacting 2-(benzo[d][1,3]dioxol-5-yl)-3-(2-chloroacetyl)-5-(1H-indol-3-yl)-2,3-dihydrooxazole-4-carboxylate with (S)-2-aminopropan-1-ol in ethanol to provide the compound of formula (III).

10. A compound of formula (I)

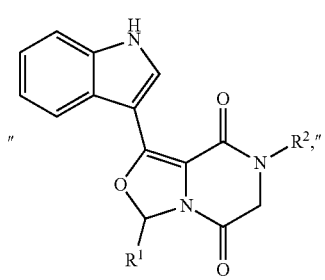

(I)

where:
R$^1$ is benzo[d][1,3]dioxolyl;
R$^2$ is CH$_2$(CH$_2$)$_n$R$^3$ or CHR$^6$CH$_2$OH;
R$^3$ is OH;
R$^6$ is CH$_3$; and
n is 1.

* * * * *